(12) United States Patent
Boone et al.

(10) Patent No.: US 11,076,821 B2
(45) Date of Patent: Aug. 3, 2021

(54) 3D-BEAM MODULATION FILTER FOR EQUALIZING DOSE AND IMAGE QUALITY IN BREAST CT

(71) Applicant: THE REGENTS OF THE UNIVERSITY OF CALIFORNIA, Oakland, CA (US)

(72) Inventors: John M. Boone, Fair Oaks, CA (US); Andrew M. Hernandez, Nevada City, CA (US); Peymon Gazi, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/779,342

(22) PCT Filed: Nov. 23, 2016

(86) PCT No.: PCT/US2016/063701
§ 371 (c)(1),
(2) Date: May 25, 2018

(87) PCT Pub. No.: WO2017/091787
PCT Pub. Date: Jun. 1, 2017

(65) Prior Publication Data
US 2018/0317867 A1  Nov. 8, 2018

Related U.S. Application Data
(60) Provisional application No. 62/260,169, filed on Nov. 25, 2015.

(51) Int. Cl.
*A61B 6/00* (2006.01)
*A61B 6/03* (2006.01)
(Continued)

(52) U.S. Cl.
CPC ............ *A61B 6/4085* (2013.01); *A61B 6/032* (2013.01); *A61B 6/0435* (2013.01); *A61B 6/405* (2013.01);
(Continued)

(58) Field of Classification Search
CPC ..... A61B 6/032; A61B 6/0435; A61B 6/4035; A61B 6/405; A61B 6/4078; A61B 6/4085;
(Continued)

(56) References Cited

U.S. PATENT DOCUMENTS

| 4,202,853 A | 5/1980 | DiTullio |
| 5,526,394 A * | 6/1996 | Siczek ................. A61B 6/4233 378/37 |

(Continued)

FOREIGN PATENT DOCUMENTS

| EP | 2305120 A1 | 4/2011 |

OTHER PUBLICATIONS

International Search Report and Written Opinion from Application No. PCT/US2016/063701, dated Feb. 2, 2017.
(Continued)

Primary Examiner — Marcus H Taningco
(74) Attorney, Agent, or Firm — Kilpatrick Townsend and Stockton LLP

(57) ABSTRACT

A size and/or shape specific 3D-beam modulation filter and a size and/or shape specific immobilizer are provided for cone-beam breast computed tomography (bCT). The immobilizer places the breast on an optimal position in the field of view of the scanner system and the 3D-beam modulation filter modulates the incident x-ray beam in the cone-angle (i.e. z-axis of the detector panel) and fan angle (i.e. x-axis of the detector panel) directions in order to improve equalization of the photon fluence incident upon the detector panel
(Continued)

and reduce unnecessary radiation dose that the breast receives. Both the immobilizer and the 3D-beam modulation filter are selected among a plurality of alternatives based on the specific shape, size and/or shape or size of the person's breast.

32 Claims, 31 Drawing Sheets

(51) Int. Cl.
*A61B 6/04* (2006.01)
*G21K 1/10* (2006.01)

(52) U.S. Cl.
CPC .......... *A61B 6/4035* (2013.01); *A61B 6/4078* (2013.01); *A61B 6/502* (2013.01); *A61B 6/5205* (2013.01); *A61B 6/544* (2013.01); *A61B 6/582* (2013.01); *A61B 6/583* (2013.01); A61B 6/5258 (2013.01); A61B 6/5294 (2013.01); *G21K 1/10* (2013.01)

(58) Field of Classification Search
CPC ..... A61B 6/502; A61B 6/5205; A61B 6/5258; A61B 6/5294; A61B 6/544; A61B 6/582; A61B 6/583; G21K 1/10
See application file for complete search history.

(56) References Cited

U.S. PATENT DOCUMENTS

| | | |
|---|---|---|
| 6,304,770 B1 | 10/2001 | Lee et al. |
| 6,480,565 B1* | 11/2002 | Ning ..................... A61B 6/032 378/20 |
| 6,618,466 B1 | 9/2003 | Ning |
| 6,950,492 B2 | 9/2005 | Besson |
| 7,864,918 B2 | 1/2011 | Schilling et al. |
| 2004/0081273 A1 | 4/2004 | Ning |
| 2005/0089135 A1 | 4/2005 | Toth et al. |
| 2008/0123816 A1 | 5/2008 | Mori et al. |
| 2008/0187095 A1* | 8/2008 | Boone .................. A61B 6/0435 378/37 |
| 2010/0080345 A1 | 4/2010 | Schilling et al. |
| 2018/0344167 A1* | 12/2018 | Xiang .................. G06T 11/003 |

OTHER PUBLICATIONS

Boone, J.M. et al, "Dedicated breast CT: radiation dose and image quality evaluation", Medical physics vol. 221, No. 3. pp. 657-667, Dec. 2001.

Boone, J.M. et al, "A comprehensive analysis of DgN (CT) coefficients for pendant-geometry cone-beam breast computed tomography", Medical physics vol. 31, No. 2, pp. 226-235, Feb. 2004.

Kwan, Alexander L.C. et al, "Evaluation of x-ray scatter properties in a dedicated cone-beam breast scanner", Medical physics vol. 32. No. 9, pp. 2967-2975, Sep. 2005.

Graham, S.A. et al., "Compensators for dose and scatter management in cone-beam computed tomography", Medical physics vol. 34, No. 7, pp. 2691-2703, Jul. 2007.

Maii, N et al., "The influence of bowtie filtration on cone-beam CT image quality", Medical physics vol. 36, No. 1, pp. 22-32, Jan. 2009.

Luck, F. et al., "Effect of shaped filter design on dose and image quality in breast CT", Physics in Medicine and Biology 58, pp. 4205-4223, May 2013.

Kontson, K et al., "Bowtie filters for dedicated breast CT: Theory and computational implementation", Medical physics vol. 42, No. 3, p. 1453-1462, Mar. 2015.

\* cited by examiner

3D-BEAM MODULATION FILTER FOR EQUALIZING DOSE AND IMAGE QUALITY IN BREAST CT

RELATED APPLICATIONS

The present application claims benefit to prior-filed provisional Application No. 62/260,169 filed on Nov. 25, 2015 entitled "3D-Beam Modulation Filter for Equalizing Dose and Image Quality in Breast CT", the content of which is incorporated herein in its entirety.

STATEMENT AS TO RIGHTS TO INVENTIONS MADE UNDER FEDERALLY SPONSORED RESEARCH AND DEVELOPMENT

This invention was made with Government support under Grant No. EB002138 awarded by the National Institutes of Health. The Government has certain rights in this invention.

BACKGROUND OF THE INVENTION

Conventional computed tomography (CT) systems for breast imaging do not account for the actual shape or size of the breast of the person. Most conventional systems emit an approximately uniform distribution of x-ray photons on the imaged object (e.g. the breast). As a result, the intensity of the x-ray beam that strikes the x-ray detector system is much lower under the thicker posterior part of the breast (closer to the chest wall) relative to the thinner anterior part of the breast, near the nipple. As a result, the intensity of the detected x-ray beam is inhomogeneous and the radiation dose is higher anteriorly relative to the posterior portion of the breast.

Most conventional multi-detector CT systems (and more recently whole body cone-beam CT systems) commonly utilize a bowtie-shaped filter to modulate the incident x-ray fluence along the fan angle direction of a detector panel. Bowtie-shaped filters may improve the performance of these systems by reducing the required detector dynamic range, reducing scatter from the edge of the person, reducing person dose, and reducing the effects of beam-hardening.

A conventional whole body CT system may include three separate bowtie-shaped filters to produce the same spectral shape and intensity at the detector using (1) a single material, (2) two different materials, and (3) to reduce the beam hardening effect in the reconstructed image by adjusting the bowtie-shaped filter thickness so that the effective attenuation for every ray is approximately the same. One dimensional bowtie filters have also been proposed for breast CT systems, assuming the breast is a circular cylinder. However, the reduction in radiation dose provided by these conventional bowtie-filters may be greatly improved if the actual breast shape of the person being imaged is considered when designing the filter.

Embodiments of the present invention solve these problems and other problems, individually and collectively.

BRIEF SUMMARY OF THE INVENTION

The present invention provides a 3D-beam modulation filter for dedicated cone-beam breast computed tomography (bCT). The filter modulates the incident x-ray beam in the cone-angle (i.e. z-axis of the detector panel) and fan angle (i.e. x-axis of the detector panel) directions in order to partially equalize the photon fluence incident upon the detector panel and to reduce the radiation levels that some parts of the breast receive. The filter attenuates x-ray intensity along the x-ray paths that are attenuated only slightly by the breast (i.e. anterior and peripheral regions of the breast), while attenuating much less of the x-ray intensity along the highly attenuating x-ray paths (i.e. the posterior and central regions of the breast). Use of the filter reduces radiation dose to the person and improves the image quality compared to conventional cone beam bCT systems, which do not use x-ray modulation in both the cone angle and fan angle directions.

Embodiments provide a mechanism that may select a 3D-beam modulation filter among a plurality of 3D-beam modulation filters based on the shape of the breast of a person. For example, embodiments may provide five different 3D-beam modulation filters designed based on actual breast geometries of a large population average over a range of women (e.g. about 215 women) with different breast shapes and sizes. For a given person, an image (e.g. an x-ray image or an optical image) of the breast may be generated to determine the actual shape of the person's breast. One of the five different 3D-beam modulation filters may be dynamically selected based on the actual breast shape using motorized wheels or translating systems. The 3D-beam modulation filter is used in bCT imaging to reduce the radiation dose received by the person and to improve the image quality of the bCT.

In some embodiments, a method for acquiring a CT image of a body part using a scanner system is provided. The method includes selecting an immobilizer among a plurality of immobilizers based on a shape or size of the body part. The method also includes selecting a 3D-beam modulation filter among a plurality of 3D-beam modulation filters based on the shape or size of the body part. The 3D-beam modulation filter is placed at a predetermined distance from an x-ray source of the scanner system. The selected immobilizer is coupled to the system. In some embodiments, the selected immobilizer may be coupled to the scanner system by attaching a first end of an attachment element to a surface of the scanner system, and attaching second end of the attachment element to the selected immobilizer. The attachment element may include a flange or a fastener. The method further includes positioning the body part in the selected immobilizer and acquiring a computed tomography (CT) image of the body part using the scanner system including the 3D-beam modulation filter. In some embodiments, acquiring the CT image of the body part further comprises collecting x-rays beams emitted from the x-ray source of the scanner system on a detector panel of the scanner system, wherein the x-ray beams emitted by the x-ray source are filtered by the 3D-beam modulation filter prior to traveling through the body part.

In some embodiments, the body part may be a breast. The 3D-beam modulation filter is designed to reduce unnecessary radiation dose towards the anterior and peripheral regions of the breast. According to various embodiments, the method may also include identifying a predetermined profile among a plurality of predetermined profiles based on the shape or size of the body part, wherein each of the plurality of 3D-beam modulation filters and each of the immobilizers are generated for one of the plurality of predetermined profiles. The method may also include forming a plurality of molds corresponding to the plurality of predetermined profiles, and producing the plurality of immobilizers using the plurality of molds. Producing the molds may also include producing a first immobilizer using a first mold corresponding to a first predetermined profile, and producing a second immobilizer using a second mold corresponding to a second predetermined profile. Embodiments allow for dynamic adjustment of the 3D-beam modulation filter prior to acquiring the computed tomography (CT) image of the body part.

According to various embodiments, the 3D-beam modulation filter may be a combined filter. In such embodiments, the method may also include selecting a bowtie-shaped filter among a plurality of bowtie-shaped filters based on the shape or size of the body part, selecting a wedge-shaped filter among a plurality of wedge-shaped filter based on the shape or size of the body part, and combining the selected bowtie-shaped filter and the selected wedge-shaped filter into the combined filter.

Embodiments may further provide a computing device including a non-transitory storage medium storing instructions, and a processor executing the instructions stored on the non-transitory storage medium to perform the method of described above.

Embodiments may also provide a computed tomography (CT) scanner system including an x-ray production system including an x-ray source emitting x-ray beams and an x-ray detector system for receiving the x-ray beams emitted by the x-ray source. The CT scanner system may also include a 3D-beam modulation filter positioned between the x-ray source and the detector system at a predetermined distance from the x-ray source. The 3D-beam modulation filter is specific to a predetermined body part shape or size. The CT scanner system may further include a gantry assembly system including a surface for receiving a body part to be imaged, and an immobilizer coupled to the gantry assembly system using one or more attachment elements. The body part being imaged may conform to the predetermined body part shape or size and the immobilizer is specific to the predetermined body part shape or size.

In some embodiments, the CT scanner system may include a scanner control computer coupled to the x-ray production system and the gantry assembly system for sending control signals to the x-ray production system and the gantry assembly system. The CT scanner system may also include a filter positioning system for selecting the 3D-beam modulation filter among a plurality of 3D-beam modulation filters based on the predetermined body part shape or size, and for positioning the 3D-beam modulation filter between the x-ray source and the detector system at the predetermined distance from the x-ray source. In some embodiments, the 3D-beam modulation filter includes a combined filter. For such embodiments, the filter positioning system is further configured to select a bowtie-shaped filter among a plurality of bowtie-shaped filters based on the predetermined body part shape or size, select a wedge-shaped filter among a plurality of wedge-shaped filter based on the predetermined body part shape or size, and combine the selected bowtie-shaped filter and the selected wedge-shaped filter into the combined filter.

According to various embodiments, the CT scanner system may also include an image acquisition computer for receiving image data from the x-ray detector system, an image reconstruction computer for reconstructing the CT image of the body part based on the image data received from the image acquisition computer, and a display for displaying the reconstructed CT image of the body part. The image reconstruction computer receives data from the scanner control computer and the image acquisition computer, the data including one or more of x-ray beam intensity data, projection images of the body part being imaged, x-ray beam emission timing data or gantry assembly system positioning data.

These and other embodiments are described in further detail below.

DETAILED DESCRIPTION OF THE INVENTION

The present invention provides a 3D-beam modulation filter that improves the image quality and reduces the x-ray exposure (e.g. radiation dose) on the breast of a person. The 3D-beam modulation filter is designed based on the specific breast shape or size of a given person. The 3D-beam modulation filter is used in breast CT (bCT) imaging to reduce the radiation dose received by the person during the examination and to improve the image quality of the bCT. The invention described herein uses a large cohort of person bCT volume datasets to design the 3D-beam modulation filters and, as such, is based on a relatively large population average over a range of women with different breast shapes and sizes. The present methodology for designing a 3D-beam modulation filter is derived from projection images measured on a bCT system, making it well suited for flexibility across many different imaging geometries, x-ray techniques, and objects being imaged. According to various embodiments, the systems and methods described herein are not limited for breast imaging but may be used in connection with various parts of a human or animal body. In addition, the 3D-beam modulation filters may be designed for many different breast sizes and a filter positioning device may allow for the selection and adjustment of the filter on a person-specific basis.

Overview of the Exemplary System

Figure 1:
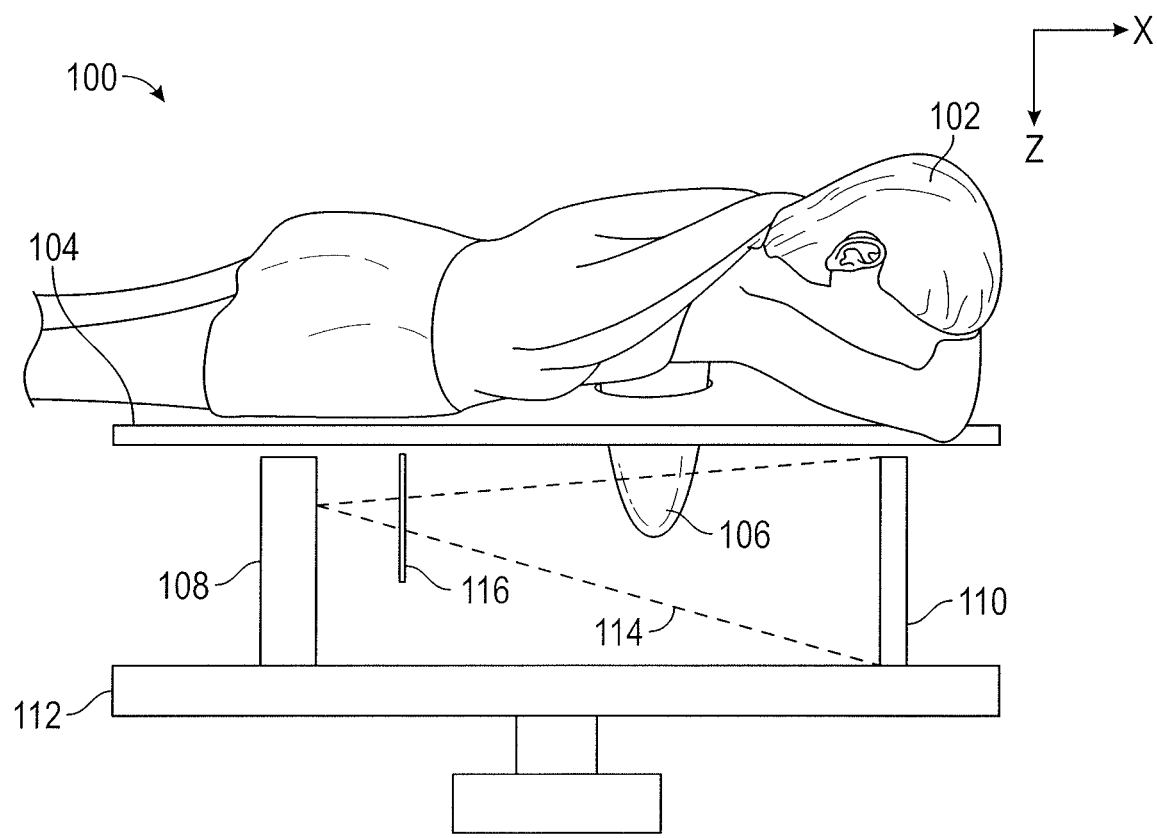
FIG. 1 illustrates an exemplary system for cone-beam breast computed tomography (bCT) in accordance with embodiments of the invention.

FIG. 1 illustrates an exemplary system 100 for cone-beam breast computed tomography (bCT) in accordance with embodiments of the invention. As illustrated in FIG. 1, a person 102 may be positioned on a table 104 in the prone position with the breast 106 to be imaged hanging pendant between an x-ray source 108 and a flat panel detector 110. The x-ray source 108 and the flat panel detector 110 are coupled to a gantry 112 that rotates around the person's body part (e.g. the breast 106) to scan the body part beneath the table 104. In some embodiments, the breast may be provided in a breast immobilizer (e.g. a breast immobilizing cone or a breast immobilization device) that positions the breast at the center of the field of view (FOV) 114. The x-ray source 108 and the flat panel detector 110 are connected to the gantry 112 that rotates around the person's breast 106 (provided in the breast immobilizer). The rotational plane of the gantry 112 is the plane of the fan angle (i.e. x-axis of the detector panel 110 as illustrated in FIG. 1).

Figure 2A:
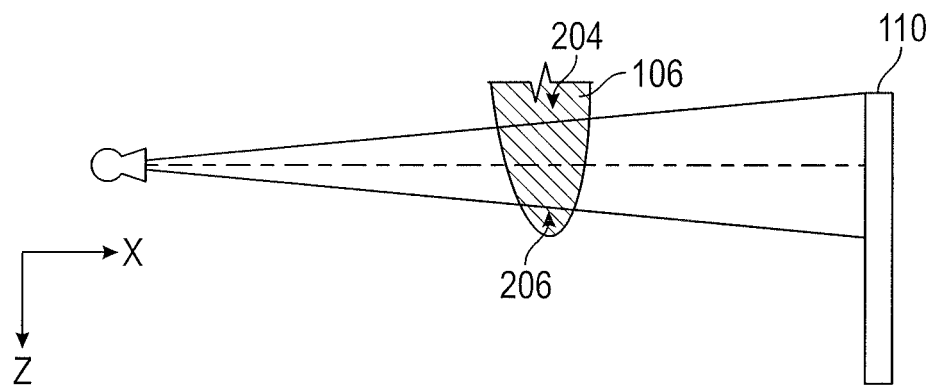
FIG. 2A illustrates x-ray beam path length location for posterior and anterior regions of the breast in the cone angle direction in accordance with embodiments of the invention.

The signal received at the detector panel 110 is dependent on the path length traveled by the photons emitted by the x-ray source 108 as they pass through the breast tissue within the detector field of view (FOV) 114. Large differences in breast thickness as a function of location along the detector panel 110 results in unequal photon fluence striking the detector 110. Given that the relative image noise is inversely proportional to the number of detected photons, the noise in the cone angle direction (i.e., z-axis of the detector panel 110 as illustrated in FIG. 1, the vertical direction of the detector panel 110) of a cone-beam projection of the breast increases towards the posterior region 204 of the breast 106 due to its greater x-ray attenuation in this relatively thick region as shown in FIG. 2A. Specifically, FIG. 2A illustrates x-ray beam path length location for posterior 204 and anterior 206 regions of the breast 106 in the cone angle direction in accordance with embodiments of the invention.

Figure 2B:
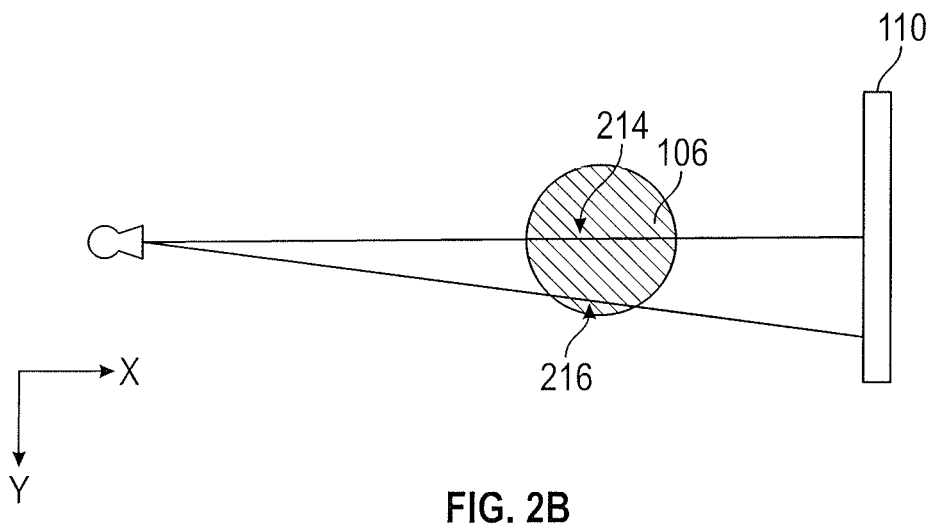
FIG. 2B illustrates x-ray beam path length location for central and peripheral regions of the breast in the fan angle direction in accordance with embodiments of the invention.

Similarly, the noise in the fan angle direction (i.e., y-axis of the detector panel 110 perpendicular to x-axis and z-axis illustrated in FIG. 1, the horizontal direction of the detector panel 110) of a cone-beam projection of the breast increases towards the central region 214 of the breast 106 due to its greater x-ray attenuation in this relatively thick region as shown in FIG. 2B. Specifically, FIG. 2B illustrates x-ray beam path length location for central 214 and peripheral 216 regions of the breast 106 in the fan angle direction in accordance with embodiments of the invention.

The highest noise levels are typically seen in the thicker central and posterior parts of the bCT images and lower noise levels are typically seen on the periphery and anterior parts of the bCT images. This is due to the reconstruction process used to compute the bCT images inherently propagating the noise.

Radiation dose coefficients in bCT are greater for smaller diameter breasts relative to larger diameter breasts based on Monte Carlo simulations of cylindrical phantoms. In reality, the breast 106 in pendant geometry (as illustrated in FIG. 1) is more of a conical shape that tapers in diameter towards the nipple. Given a relatively uniform x-ray spectrum incident upon the breast 106, a conical shaped breast will receive a slightly higher radiation dose anteriorly (e.g. at and around the nipple) and lower radiation dose posteriorly (e.g. closer to the chest wall). Thus, a 3D-beam modulation filter 116 is designed in the present invention to reduce the unnecessary dose towards the anterior and peripheral regions of the breast, respectively, where the higher detected signal (i.e. lower noise) does not substantially contribute to improved image quality. As illustrated in FIG. 1, the 3D-beam modulation filter 116 may be positioned between the x-ray source 108 and the breast 106, at a predetermined distance from the x-ray source 108. According to an exemplary embodiment, the predetermined distance between the 3D-beam modulation filter 116 and the x-ray source 108 may be about 10 cm. However, the predetermined distance is not limited to the exemplary embodiment and can be any suitable distance that allows for radiation dose reduction on the person without compromising on the image quality.

Figure 3:
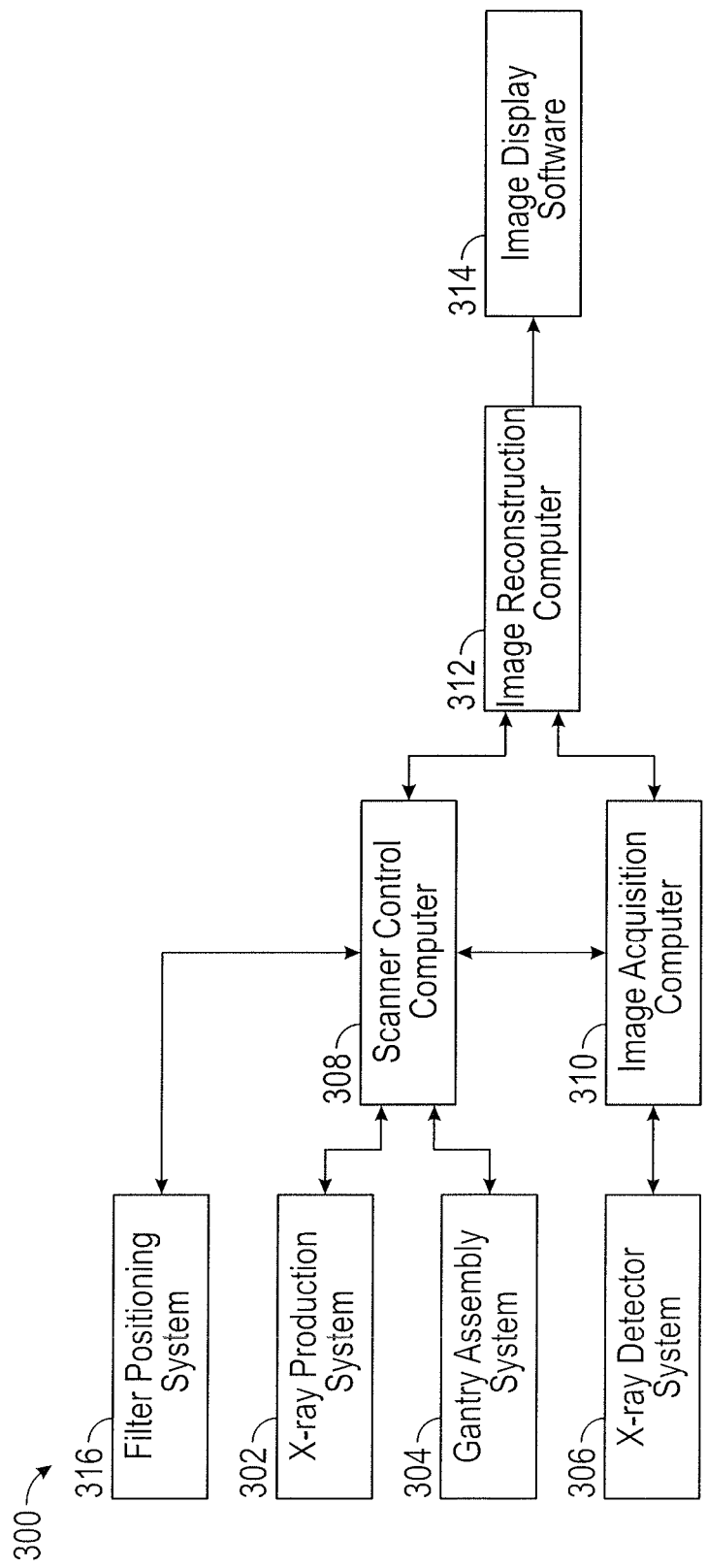
FIG. 3. illustrates an exemplary system 300 for acquiring bCT images using a 3D-beam modulation filter according to various embodiments of the present invention.

FIG. 3 illustrates an exemplary system 300 for acquiring bCT images using a 3D-beam modulation filter according to various embodiments of the present invention. The system 300 includes imaging and computing modules as well as the components of the exemplary system 100 for cone-beam breast computed tomography (bCT) illustrated in FIG. 1. Specifically, the system 300 includes an x-ray production system (e.g. the x-ray source 108), a gantry assembly system 304 (e.g. the gantry 112 and the table 104), an x-ray detector system 306 (e.g. the detector panel 110), and a scanner control computer 308. The scanner computer 308 may send control signals to the x-ray production system 302 to adjust the intensity and/or timing of the x-ray beams produced by the x-ray production system 302. The scanner computer 308 may also send control signals to the gantry assembly 304 to correctly position the person relative to the x-ray production system 302. When the desired configuration is achieved, the scanner control computer 308 may send a control signal to the x-ray production system 302 to start the x-ray beam production by the x-ray production system 302.

According to various embodiments, the system 300 may also include a filter positioning system 316. The filter positioning system 316 may change the 3D-beam modulation filter to be used during the scanning process based on the breast class of the user. As further described below, embodiments of the present invention are directed to forming a dedicated 3D-beam modulation filter for each identified breast class. Accordingly, a first 3D-beam modulation filter may be used for persons having a first breast class and a second 3D-beam modulation filter for persons having a second breast class. The scanner computer system 308 may receive a determination of the person's breast class (e.g. through user input or through input from an evaluating system that evaluates person's breast to determine the breast profile) and send a signal to the filter positioning system 316 to select the 3D-beam modulation filter corresponding the person's breast class among the plurality of 3D-beam modulation filters, and place the selected 3D-beam modulation filter at a predetermined distance from the x-ray production system 302, between the x-ray production system 302 and x-ray detector system 306.

According to various embodiments, the scanner computer system 308 may send signals to the filter positioning system 316 and the gantry assembly system 304 to adjust the respective positions of the 3D-beam modulation filter and the gantry if the person's breast is not at an optimal location within the field of view of the laser beam. For example, the position of the 3D-beam modulation filter and the gantry may be adjusted according to a first person with a first breast class. When a second person is placed on the gantry, adjustment to the placement of the filter and/or the gantry may be necessary. If the second person has a second breast class, then the scanner control computer 308 may instruct the filter positioning system 316 to change the filter to the 3D-beam modulation filter corresponding the second breast class. On the other hand, even if the second person has the first breast class (e.g. the same breast class as the previous person), the second person may be lighter/heavier than the previous person thus may result in the table being pressed higher/lower than the previous person. This may result in the second person's breast not being optimally located within the field of view of the laser beam. In such cases, the scanner control computer 308 may instruct the gantry assembly system 304 to go lower/higher to place the breast within the field of view of the laser beam.

According to various embodiments, the system 300 may also include an image acquisition computer 310, an image reconstruction computer 312, and an image display software 314. After the x-ray production system 302 starts the x-ray beam production, the scanner control computer 308 may notify the image acquisition computer 310 to acquire one or more x-ray images of the person's body part (e.g. breast). The image acquisition computer 310 may receive or acquire (e.g. pull) the image data from the x-ray detector system 306. The image acquisition computer 310 may send the acquired image data to the image reconstruction computer 312. The image reconstruction computer 312 may also receive data (e.g. x-ray beam intensity data, x-ray beam emission timing data, the gantry assembly system positioning data, etc.) from the scanner control computer 308. The image reconstruction computer 312 may reconstruct the CT image of the person's breast based on the image data received from the image acquisition computer 310 and display the reconstructed image using an image display software 314 on a display device. According to various embodiments, the image display software 314 may be provided on the image reconstruction computer 312, on a different computer or on a remote server (e.g. cloud storage).

The 3D-beam modulation filter 116 may compensate for the differences in thickness of the breast 106 and equalize the attenuation of the signal levels at the detector 110. However, for the 3D-beam modulation filter 116 to work properly, the exact location of the breast 106 with respect to the x-ray source 108 and the detector 110 needs to be determined and/or known. The breast 106 may be placed at a predetermined (e.g. known) position by using a breast immobilizer, discussed below. A series of breast-immobilizing molds are produced from a large cohort of breast CT volume datasets of women with different breast shapes and sizes. The breast immobilizers help to conform the breast to be imaged to be centered in the field of view, and positioned to optimally exploit the shape of the 3D-beam modulation filter.

The purpose of the breast immobilizer is to gently force the pendant breast to conform to the shape of the breast immobilizer. The breast immobilizer corresponding to the person's breast size/category may be positioned over the hole on the table where the breast to be imaged is placed. The 3D-beam modulation filter works together with the size-specific breast immobilizer to equalize the signal levels at the detector and reduce radiation dose in the anterior region and periphery of the breast.

The breast immobilizers are generated using a plurality of realistic breast-shaped phantoms that are pre-defined shapes formed using the large cohort of breast CT volume datasets of women with different breast shapes and sizes. For a given person, the breast is assumed to conform to one of the pre-defined breast-shaped phantoms. The breast-shaped phantoms are used as molds for creating the breast immobilizers.

Identification of Breast Classes

Figure 4A:
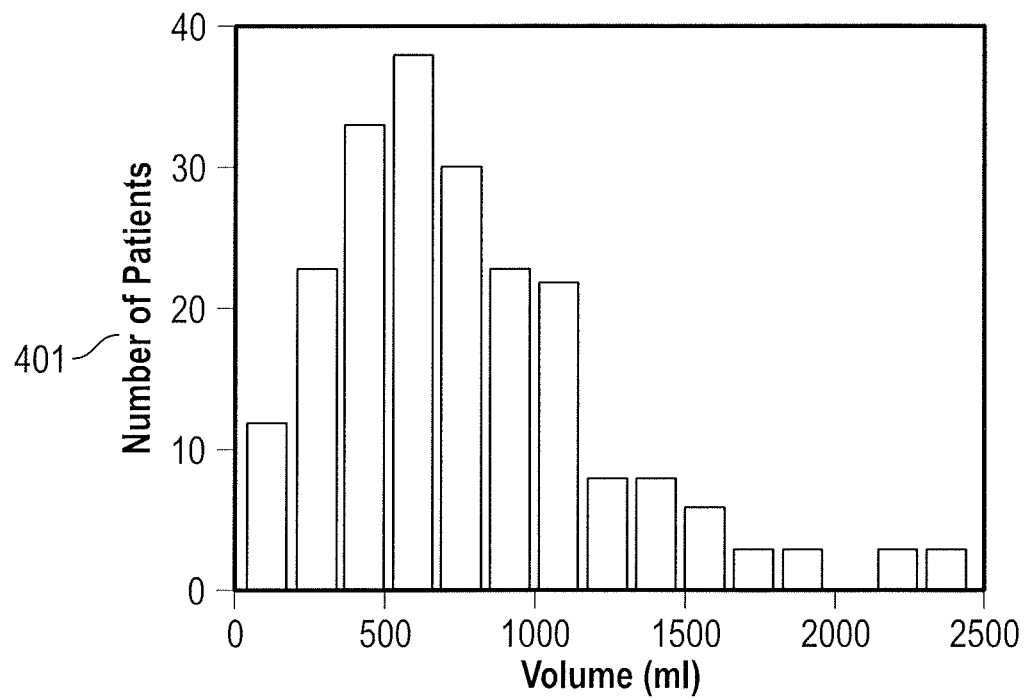
FIG. 4A illustrates a histogram of breast volumes from a large cohort of bCT volume data sets of a plurality of actual persons according to various embodiments of the present invention.

FIG. 4A shows a histogram 400 of breast volumes from a large cohort of breast CT volume data sets of a plurality of (e.g. 215) actual persons. One of ordinary skill in the art will appreciate that the number of experiment subjects may be modified as long as a statistically significant group is analyzed.

As used herein, the breast CT volume data set may include a complete 3D reconstruction of the object (e.g. body part, breast) using a plurality of projection images (e.g. about 500 projection images) from a plurality of x-ray source and detector panel positions (e.g. about 500 positions).

As used herein, a projection image may include a single image of an object (e.g. body part) for a single x-ray source and detector panel position.

According to exemplary embodiments, the total breast volume of 215 dedicated breast CT volume data sets may be classified into a plurality of percentile groups, e.g. $0\text{-}20^{th}$, $20\text{-}40^{th}$, $40\text{-}60^{th}$, $60\text{-}80^{th}$, and $80\text{-}100^{th}$ percentiles, corresponding to breast volumes, e.g. x-small (V1), small (V2), medium (V3), large (V4), and x-large (V5) breast volumes. Thus, the gathered data may be classified into five main classes based on the identified five percentile groups. According to various embodiments, the data may be classified into multiple classes based on volume, size, shape or any other determining factor. In the exemplary embodiment illustrated in FIG. 4A, the data is classified by volume. A volume index (e.g. V1, V2, V3, V4 and V5) may be assigned to each identified breast class, each breast class corresponding to the average effective diameter profile within each of the five percentile group.

Figure 4B:
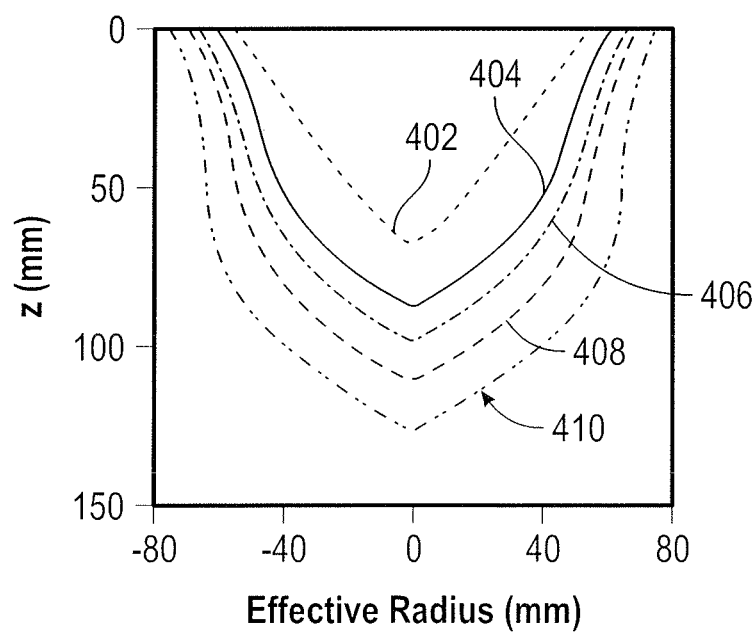
FIG. 4B illustrates average radius profiles for a plurality of subsets of breast sizes determined based on the data illustrated in FIG. 4A according to various embodiments of the present invention.

According to various embodiments, average effective radius profiles may be measured within each of the breast classes V1-V5. The radius profile measurements may begin at the $1^{st}$ coronal slice containing no chest wall artifacts and end at the last coronal slice containing the person's nipple. FIG. 4B illustrates average radius profiles 402, 404, 406, 408, 410 for a plurality of subsets of breast sizes (i.e. each of the breast classes V1-V5) determined based on the data illustrated in FIG. 4A. The average radius profiles 402, 404, 406, 408, 410 may form the basis for generating a breast phantom for each of the identified breast classes. For example, the average radius profile 402 corresponds to the breast class V1 for x-small breast size, the average radius profile 404 corresponds to the breast class V2 for small breast size, the average radius profile 406 corresponds to the breast class V3 for medium breast size, the average radius profile 408 corresponds to the breast class V4 for large breast size, and the average radius profile 410 corresponds to the breast class V5 for x-large breast size.

Each breast class may be associated with specific characteristics such as chest wall diameter, breast length, breast volume, etc. The value for a given characteristic may correspond to average value of that characteristic for each member in the breast class. Table I illustrates the average chest wall diameter, the average length, the average volume and the average volumetric growth factor (VGF) for each of the percentile groups corresponding to the breast classes identified by volume index V1-V5. One of ordinary skill in the art will appreciate that the data may be categorized into any number of groups and based on any relevant criteria. The use of 5 groups based on percentile grouping is provided for illustrative purposes only and should not be construed as limiting.

TABLE 1

Properties of identified breast volumes

| Size Index | Chest Wall Diameter (mm) | Length (mm) | Volume (ml) | VGF (%) |
|---|---|---|---|---|
| V1 | 108.2 | 54 | 251.4 [26.0-395.0] | 22.2 |
| V2 | 121.6 | 80 | 499.4 [395.0-586.5] | 16.4 |
| V3 | 132.1 | 89 | 680.4 [586.5-802.1] | 13.2 |
| V4 | 138.6 | 99 | 928.2 [802.1-1078.8] | 10.5 |
| V5 | 149.2 | 106 | 1505.3 [1078.8-2450.5] | 13.5 |

One of ordinary skill in the art will appreciate that the grouping provided herein is for illustrative purposes and that the data may be classified into more or less volume-classified groups. Moreover, the effective diameter profiles may be classified by other anatomical metrics besides volume (i.e. breast diameter). A breast immobilizer (e.g. breast immobilizing mold) and a 3D-beam modulation filter of a given material (e.g. aluminum, copper, titanium) may be generated for each breast class.

Breast Phantoms and Breast Immobilizers

Figure 5:
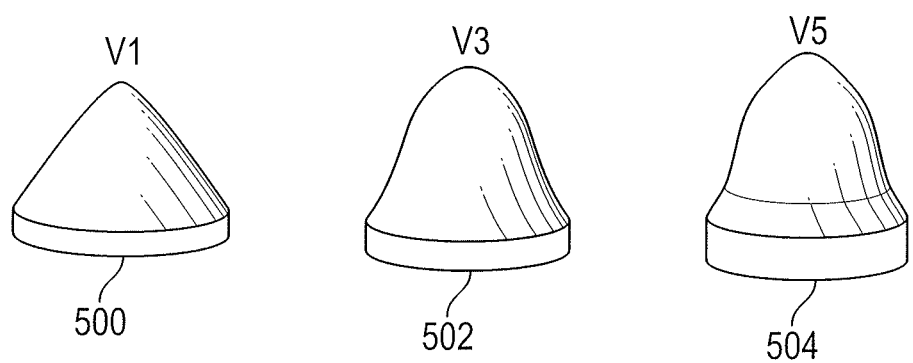
FIG. 5 illustrates exemplary breast phantoms for breast class V1, breast class V3 and breast class V5 (identified in FIGS. 4B-4C) according to various embodiments of the present invention.

The effective radius profiles 402, 404, 406, 408, 410 may be used to fabricate breast phantoms, e.g. polyethylene breast phantoms, for breast classes V1, V2, V3, V4 and V5, that represent the realistic breast volume and shape for each of the breast classes. Exemplary polyethylene phantoms for breast class V1 500, breast class V3 502 and breast class V5 504 are illustrated in FIG. 5. The phantoms illustrated in FIG. 5 are not drawn to scale. One of ordinary skill in the art would appreciate that the phantom for breast class V5 504 (i.e. phantom for x-large volume) is larger than both the phantom for breast class V1 500 (i.e. phantom for x-small volume) and the phantom for breast class V3 502 (i.e. phantom for medium volume). Similarly, the phantom for breast class V3 502 (i.e. phantom for medium volume) is larger than the phantom for breast class V1 500 (i.e. phantom for x-small volume).

Figure 6:
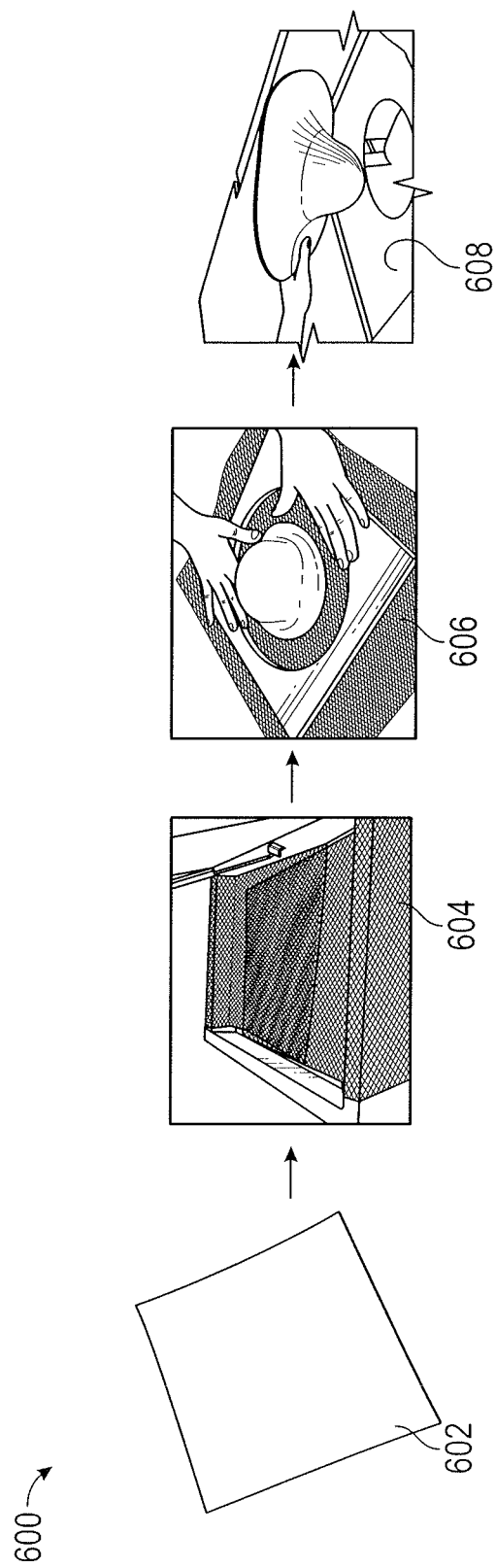
FIG. 6 illustrates a workflow for fabricating breast immobilizers using the breast phantoms as molds in accordance with embodiments of the invention.

As provided above, the phantoms may then be used to form the breast immobilizers. For example, a breast immobilizer corresponding to each one of the identified breast classes may be formed. FIG. 6 illustrates a workflow 600 for fabricating breast immobilizers using the breast phantoms as molds. At a first step, a sheet of moldable material (e.g. a thermoplastic sheet) 602 may be placed in a hot molding environment (e.g. hot water bath) 604 to be softened. The softened sheet of moldable material may be placed over one of the phantoms for breast classes V1-V5 for the molding process 606. The softened sheet of moldable material may take the shape of the phantom. When set (e.g. by being cured or any other method), the molded sheet of moldable material may form the breast immobilizer 608 corresponding to the phantom/breast class. According to various embodiments, a breast immobilizer may be formed for each breast class phantom (e.g. V1-V5). The breast immobilizer may optimize the effect of the 3D-beam modulation filter by containing the person's breast to a pre-determined shape and location.

Figure 7A:
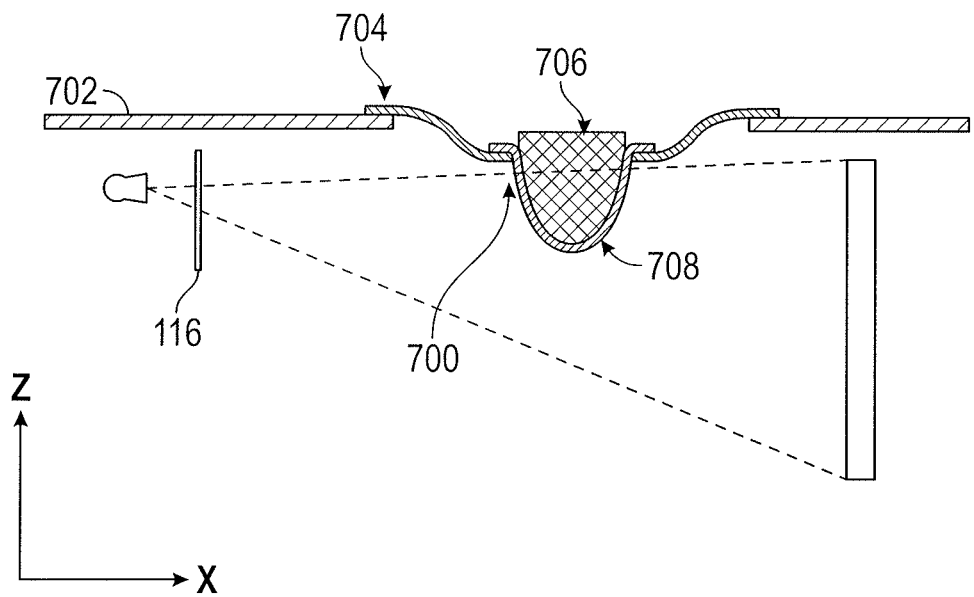
FIG. 7A illustrates a schematic of the breast immobilization device incorporated on a tabletop of a bCT system in accordance with embodiments of the invention.

FIG. 7A illustrates a schematic of the breast immobilization device 700 incorporated on the tabletop 702 of a bCT system. The immobilization device 700 may include attachment elements 704 and a breast immobilizer 708 for placing the person's chest into the x-ray source field of view (FOV) to maximize chest wall coverage. A selected thermoplastic immobilizer (e.g. breast immobilizer) 708 may be attached to the tabletop 702 of the bCT system using one or more attachment elements 704 (e.g. a flange, a neoprene flange, a fastener, a hook-and-loop fastener, etc.). According to some embodiments, the thermoplastic immobilizer 708 may be perforated. When the person's breast is placed in the thermoplastic immobilizer 708, the perforation holes may allow for a visual inspection of the goodness of fit between the breast and the thermoplastic immobilizer 708. For example, if the breast protrudes through the holes, a larger size thermoplastic immobilizer 708 may be required. Similarly, if there is a gap between the surface of the thermoplastic immobilizer 708 and the outer surface of the person's breast, a smaller size thermoplastic immobilizer 708 may be required. According to various embodiments, the check for the immobilizer fit may be performed by a laser-based system which may scan the immobilizer to detect protruding skin or a void just beneath the immobilizer surface which can then be compared to a threshold. The system may provide a recommendation to change the immobilizer based on the input from the laser detection system. Alternatively, the check for the immobilizer fit may be performed by a person, such as the x-ray technician.

Figure 7B:
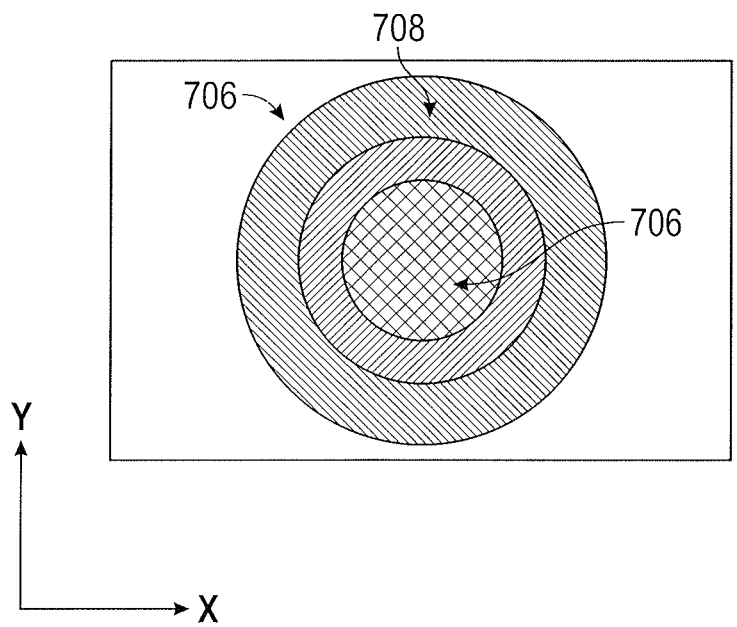
FIG. 7B illustrates a top view of the breast immobilization device illustrated in FIG. 7A in accordance with embodiments of the invention.

According to various embodiments, several different attachment elements 704 with different mechanical properties may be employed depending on the person's body habitus, for the purpose of both suspending the person's breast and chest wall into the scanner field of view (FOV) and simultaneously holding back tissue that is not of interest for the bCT acquisition. In some embodiments, the attachment element 704 may be permanently attached to the tabletop 702 of the bCT system. The breast immobilizer 708 may be coupled to the tabletop 702 by way of the attachment element 704. For example, a first end of the attachment element 704 may be attached to the tabletop 702 of the bCT system while a second end, opposite from the first end, of the attachment element 704 may be attached to the breast immobilizer 708. The thermoplastic breast immobilizer 708 may be replaced depending on the volume and shape of the person's breast by being detached from the attachment element 704 such that any one of the previously formed breast immobilizers (e.g. for profiles V1-V5) may be attached to the tabletop 102 via the attachment element 704. In the exemplary embodiment illustrated in FIG. 7A, a breast phantom 706 may be placed in the breast immobilizer 708. FIG. 7B illustrates a top view of the breast immobilization device 700 including the attachment element 704, the breast immobilizer 708 and the phantom 706 placed in the breast immobilizer 708.

Using the system setup illustrated in FIG. 7A, the breast phantoms may then be used to design different 3D-beam modulation filters such that each 3D-beam modulation filter perfectly matches the shape of each breast phantom, as discussed below.

Design of 3D-Beam Modulation Filter

The breast phantoms (e.g. phantoms for breast classes V1-V5) may be used to design five size-specific 3D-beam modulation filters. The filter design for a specific bCT scanner may depend on the system geometry and the x-ray technique of the scanner system. According to various embodiments, projection images may be obtained on the bCT system being analyzed with the breast phantom placed at the scanner isocenter.

Figure 8:
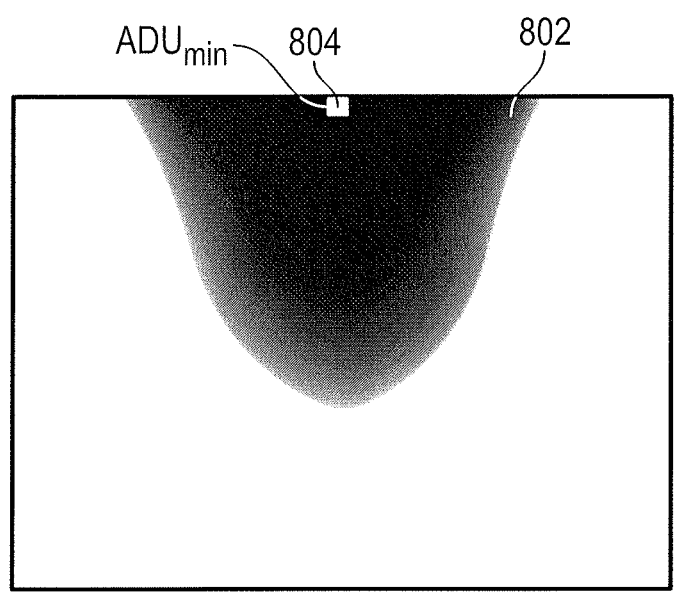
FIG. 8 illustrates a projection image of the breast phantom corresponding to the breast class V3 acquired on a bCT scanner using the breast immobilization device illustrated in FIGS. 7A-7B in accordance with embodiments of the invention.

FIG. 8 illustrates a projection image 802 of the phantom (without the breast immobilizer) corresponding to the breast class V3 at 65 kV with inherent filtration of 0.5 mm titanium filter acquired on a bCT scanner. The minimum detected signal ($ADU_{min}$) 804, measured in arbitrary detector unit (ADU), may be used as a normalization factor for signal equalization. $ADU_{min}$ value may be within the dynamic range of the detector panel. In some embodiments, $ADU_{min}$ value may be near the upper limit of the dynamic range of the detector panel such that the signal is not quantum noise limited. As shown in FIG. 8, the dexel location of $ADU_{min}$ coincides with the thickest region of the breast at the posterior edge. If the entire projection image was perfectly equalized, all detector elements (i.e. dexels) would be equal to $ADU_{min}$.

Figure 9A:
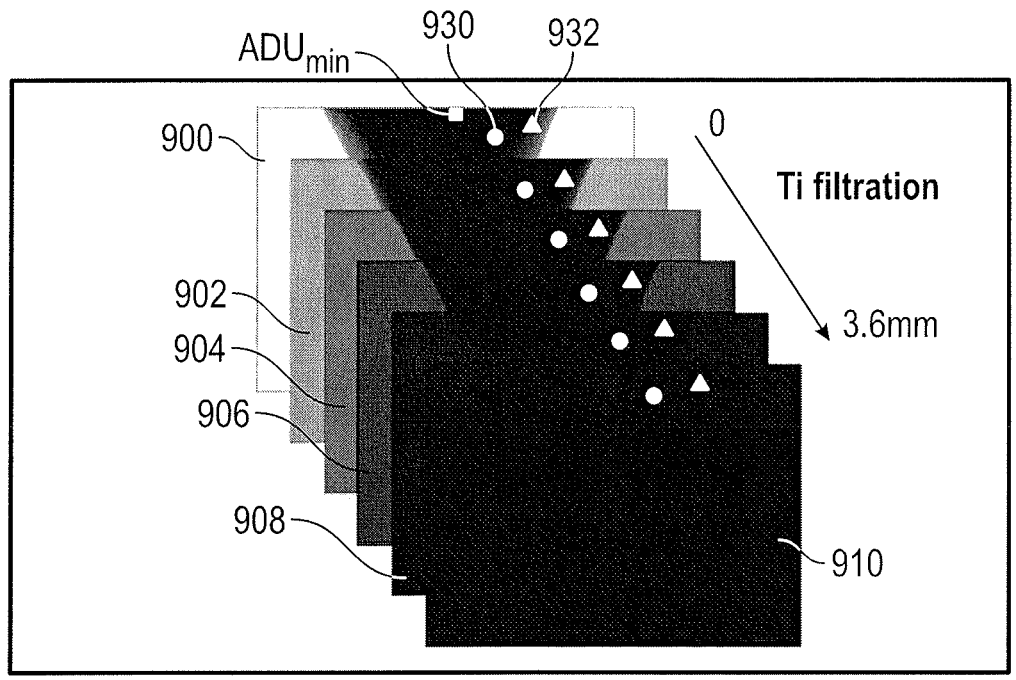
FIG. 9A illustrates a sequence of six projection images acquired using filters made of a selected filtration material (e.g. titanium) with increasing thickness in accordance with embodiments of the invention.

A plurality of projection images may be acquired with increasing thicknesses of filtration material until the ADU value in every dexel is equal to or less than $ADU_{min}$. FIG. 9A illustrates a sequence of six projection images 900, 902, 904, 906, 908 and 910 acquired using filters made of a selected filtration material (e.g. Grade-5 titanium alloy) with thickness increasing from 0 mm to 3.6 mm, respectively.

Figure 9B:
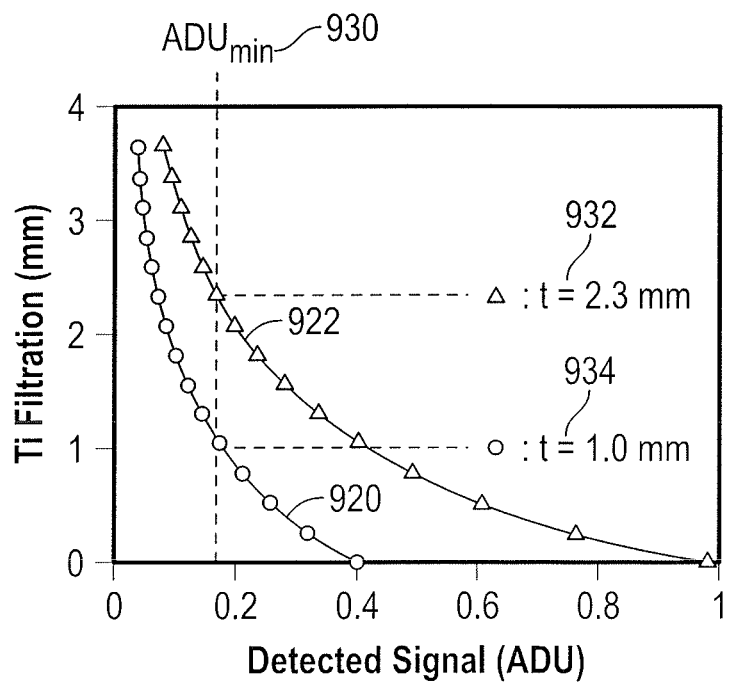
FIG. 9B illustrates plots showing the added filtration as a function of arbitrary detector unit (ADU) for two selected detector elements "dexels" of the detector panel within the entire sequence of projection images illustrated in FIG. 9A in accordance with embodiments of the invention.

The added filtration as a function of ADU may be plotted for each dexel within the entire sequence of projection images 900-910. Respective curves 920 and 922 corresponding to two exemplary dexel elements 930 and 932 are shown in FIG. 9B. The circle and triangle markers correspond to the individual dexel elements 930 and 932 illustrated in FIG. 9A. Similar curves may be plotted for each detector element (i.e. dexel) to determine the thickness of the 3D-beam modulation filter for a specific detector element. For example, if a region of interest is closer to the nipple of the breast, a first thickness may be selected for the filter. On the other hand, if the region of interest is closer to the chest wall, a second thickness (different than the first thickness) may be selected for the filter. The curves may be interpolated for the detected signal equal to $ADU_{min}$ 930 to calculate the amount of filtration 932 and 934 each ray needs to pass through as the ray originates from the focal spot to reach the particular dexel of interest.

Figure 10:
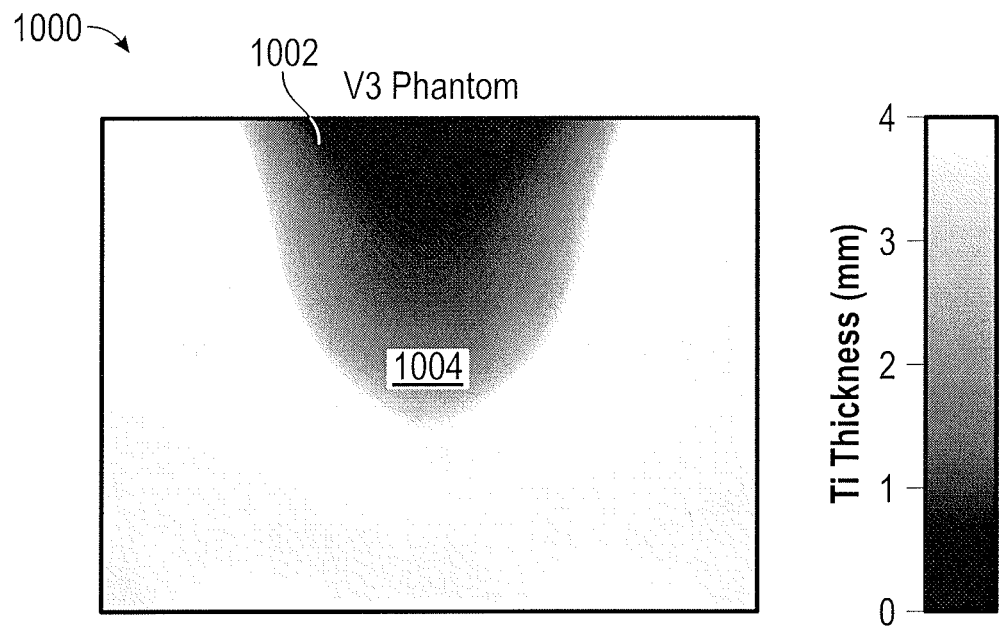
FIG. 10 illustrates an exemplary 3D-beam modulation filter thickness map resulting from repeating the process shown in FIGS. 9A-9B for all dexels of the detector panel in accordance with embodiments of the invention.

FIG. 10 shows an example of the 3D-beam modulation filter thickness map 1000 resulting from repeating the process shown in FIGS. 9A-9B for all dexels within the detector panel. The thickest region of breast is at the central-posterior edge 1002 of the breast near the chest wall. This region requires less filtration than the region closer to the anterior edge 1004 of the breast near the nipple where the projection thickness is much thinner.

Figure 11:
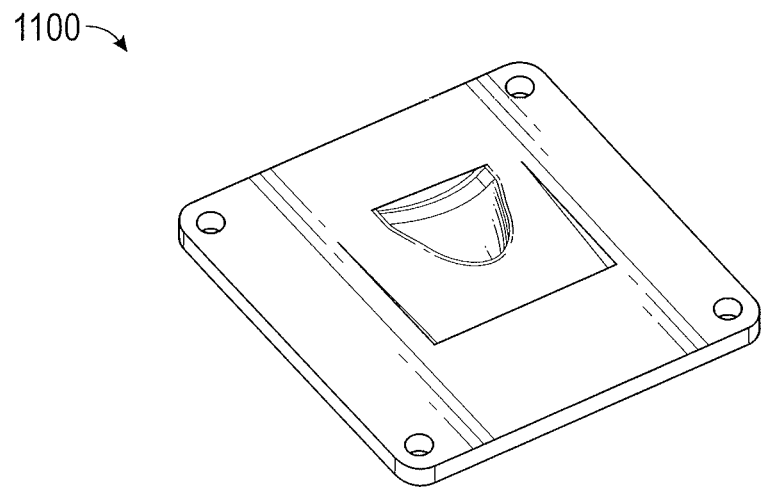
FIG. 11 illustrates an exemplary CAD model of the 3D-beam modulation filter design in accordance with embodiments of the invention.

FIG. 11 illustrates an exemplary CAD model 1100 of the 3D-beam modulation filter design according to various embodiments. The image-derived design for the 3D-beam modulation filter discussed herein is a robust method in that the resulting 3D-beam modulation filter design inherently includes the effects of the particular scanner geometry, x-ray beam hardening, object scatter, and differences in detector spectral response. One of ordinary skill in the art will appreciate that the same design method may be applied to any breast phantom size and any filtration material of interest. The design method can also be applied to other anatomical object on a person for applications outside of breast imaging.

According to various embodiments, a 3D-beam modulation filter may be used to generate an image that almost looks gray except for a fine structure (e.g. lesion of interest) detected in the woman's breast. That is, in some embodiments, an equalization filter may be designed to completely flatten the image and make it almost homogeneous exposure at the detector. The results shown in FIG. 10 assumes that a perfectly uniform detected signal is desired across the entire detector panel. However, this assumption may have adverse effects on the reconstructed image quality, mainly beam hardening artifacts and contrast-to-noise degradation. To address this issue, the 3D-beam modulation filter thickness map illustrated in FIG. 10 may be adjusted such that signal equalization is less aggressive.

Figure 12B:
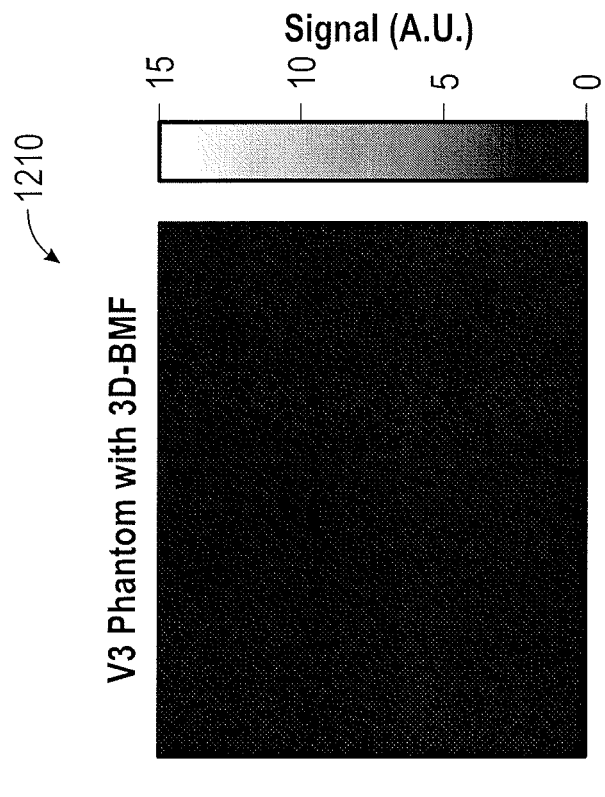
FIG. 12B illustrates Monte Carlo simulation results for a projection of the V3 phantom on the detector panel when the 3D-beam modulation filter is used in accordance with embodiments of the invention.
Figure 12A:
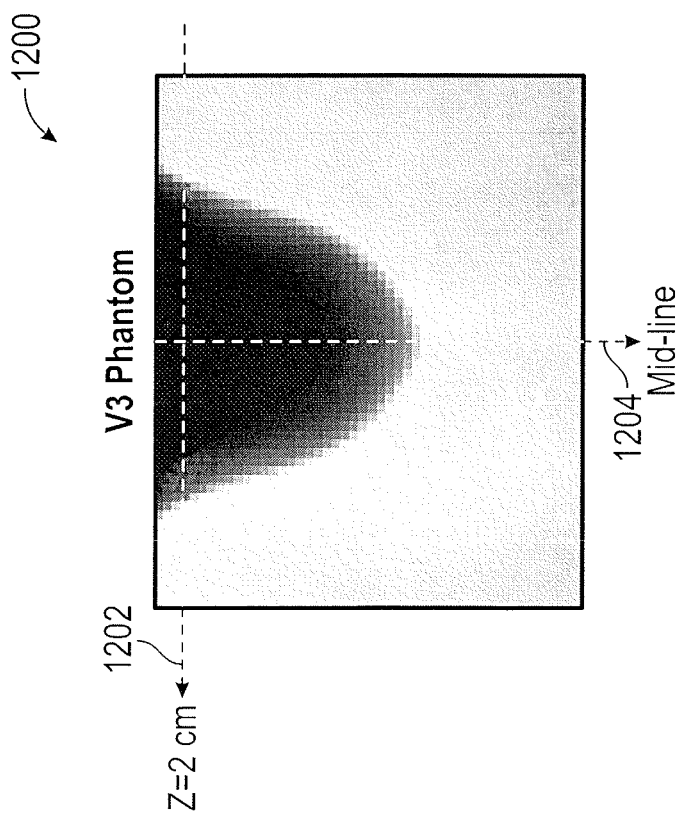
FIG. 12A illustrates Monte Carlo simulation results for a projection of the V3 phantom on the detector panel when the 3D-beam modulation filter is not used in accordance with embodiments of the invention.

Once the 3D-beam modulation filter is designed, a simulation technique such as Monte Carlo simulation may be used to estimate the performance of the resulting 3D-beam modulation filter. FIGS. 12A-12B illustrate Monte Carlo simulation results for projection images of the V3 phantom. FIG. 12A illustrates Monte Carlo simulation results 1200 for projection images of a V3 breast phantom on the detector panel without using a 3D-beam modulation filter. FIG. 12B illustrates Monte Carlo simulation results 1210 for projection images of a V3 breast phantom on the detector panel using a 3D-beam modulation filter. The simulation results 1200 and 1210 may be normalized to $ADU_{min}$ and displayed using the same color scale.

FIGS. 12A-12B illustrate the large reduction in dynamic range requirement of the detector with introduction of the 3D-beam modulation filter. Specifically, FIG. 12A shows the image of the V3 phantom acquired without using a filter. In this configuration the dexels within the breast phantom silhouette need to have a high enough detected signal to not be dominated by quantum noise and therefore results in high noise levels in the reconstructed images as discussed previously. The dexel elements outside of the breast silhouette simultaneously need to be below the saturation level for that detector panel. This configuration (e.g. the image illustrated in FIG. 12A) results in a large dynamic range requirement for the flat panel detector. On the other hand, the image illustrated in FIG. 12B requires a detector panel with much less of a dynamic range requirement.

Figure 13B:
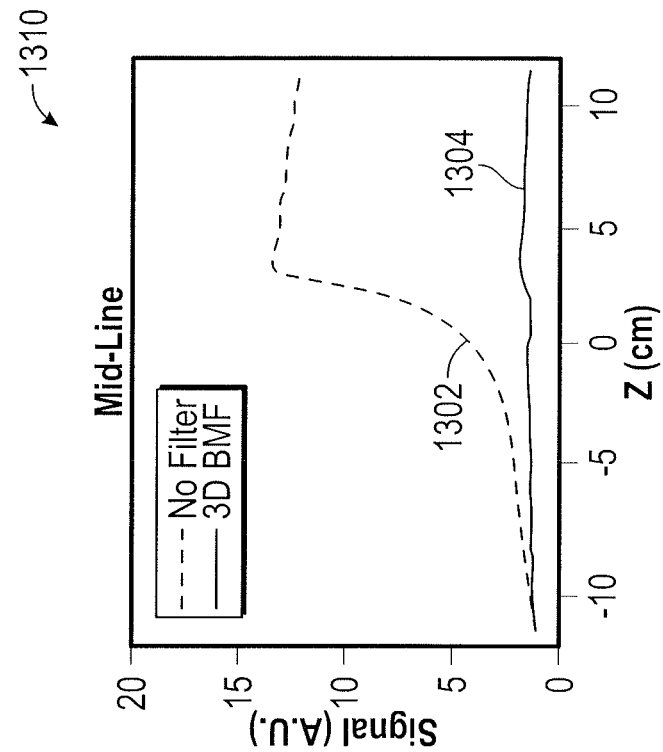
FIG. 13B illustrates comparison of a first line profile (without using a filter) and a second line profile (using a filter) through the simulated projection images along the vertical dimension shown in FIG. 12A.
Figure 13A:
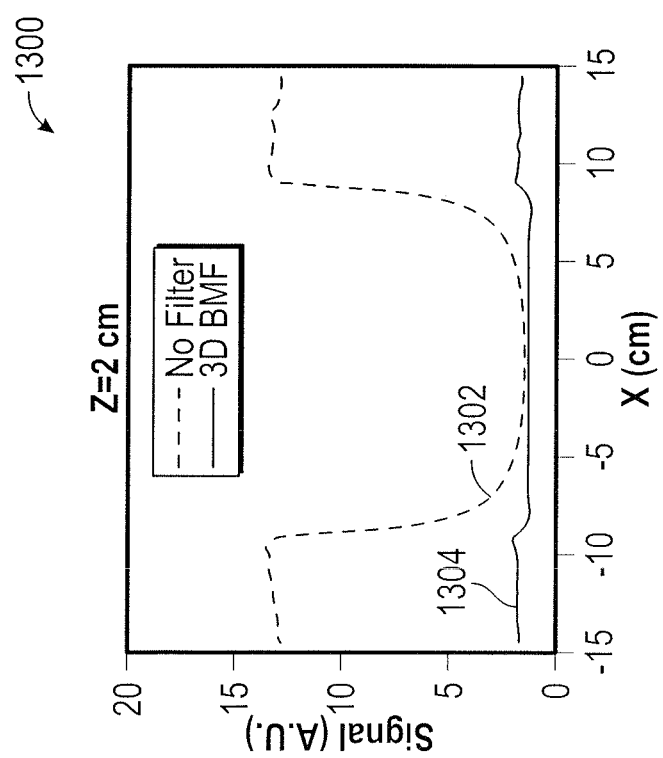
FIG. 13A illustrates comparison of a first line profile (without using a filter) and a second line profile (using a filter) through the simulated projection images along the horizontal dimension shown in FIG. 12A.

FIGS. 13A-13B illustrate comparison of line profiles through the simulated projection images shown in FIGS. 12A-12B, respectively. FIG. 13A illustrates comparison 1300 of a line profile 1302 (without using a filter) and a line profile 1304 (using a filter) through the simulated projection images along the horizontal dimension 1202 (i.e. z=2 cm from the chest wall) shown in FIG. 12A. FIG. 13B illustrates comparison 1310 of a line profile 1302 (without using a filter) and a line profile 1304 (using a filter) through the simulated projection images along the vertical dimension 1204 (i.e. midline of the breast) shown in FIG. 12A. FIGS. 13A-13B further validate a substantial flattening of the projected profile at the periphery (FIG. 13A) and anterior (FIG. 13B) region of the breast.

Figure 14B:
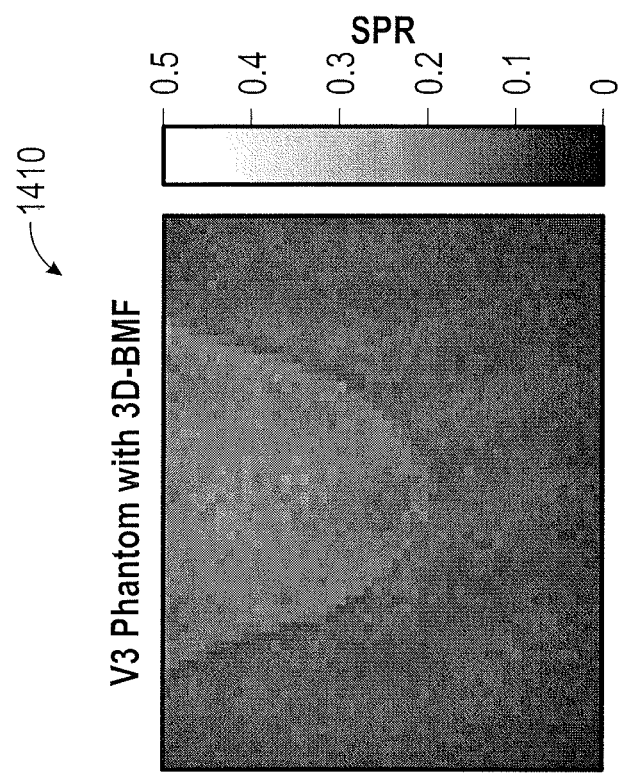
FIG. 14B illustrates Monte Carlo simulation estimations of the scatter-to-primary ratio (SPR) using a 3D-beam modulation filter in accordance with embodiments of the invention.
Figure 14A:
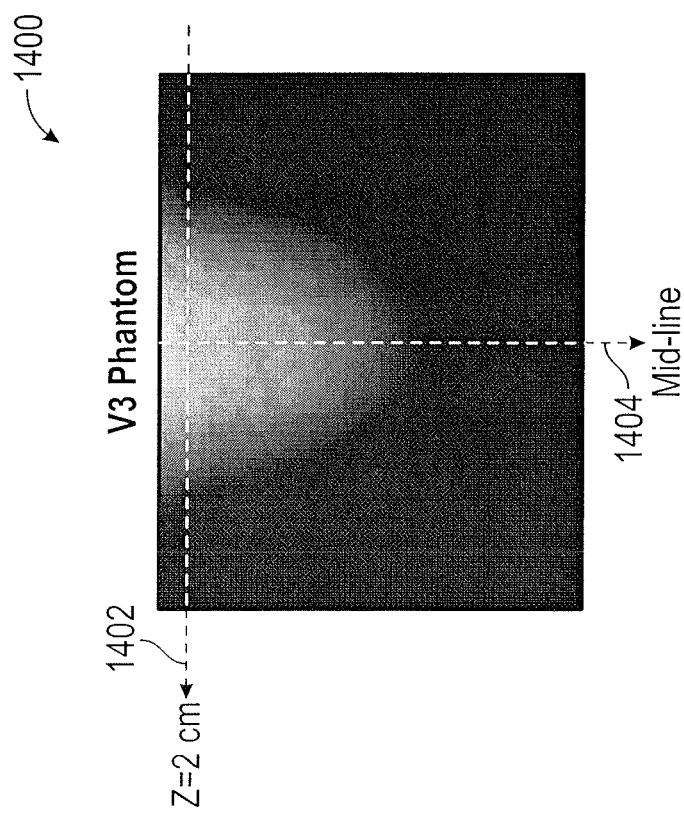
FIG. 14A illustrates Monte Carlo simulation estimations of the scatter-to-primary ratio (SPR) without using a 3D-beam modulation filter in accordance with embodiments of the invention.

Another important metric in assessing the impact of the 3D-beam modulation filter is the amount of scatter in each projection image which results in increased noise levels in the reconstructed bCT volume data sets. The scatter-to-primary ratio (SPR) is the ADU resulting from scatter (single or multiple events) divided by the ADU resulting from only primary incident radiation. FIGS. 14A-14B illustrate the Monte Carlo simulation estimations of the scatter-to-primary ratio (SPR) demonstrating an overall reduction in the SPR near the center of the breast. FIG. 14A illustrates the Monte Carlo simulation estimations of the SPR 1400 with no 3D-beam modulation filter. FIG. 14B illustrates the Monte Carlo simulation estimations of the SPR 1410 with the 3D-beam modulation filter. The average SPR within a 1 cm×1 cm square region at the posterior, mid-line region of the projection image was reduced by 31% after introducing the 3D-beam modulation filter.

Figure 15B:
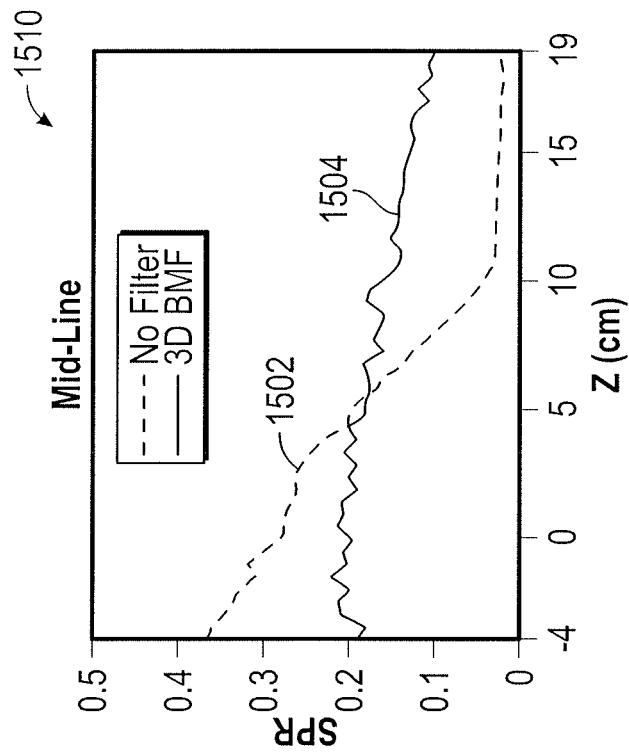
FIG. 15B illustrates comparison of a first line profile (without using a filter) and a second line profile (using a filter) through the simulated SPR maps along the vertical dimension shown in FIG. 14A.
Figure 15A:
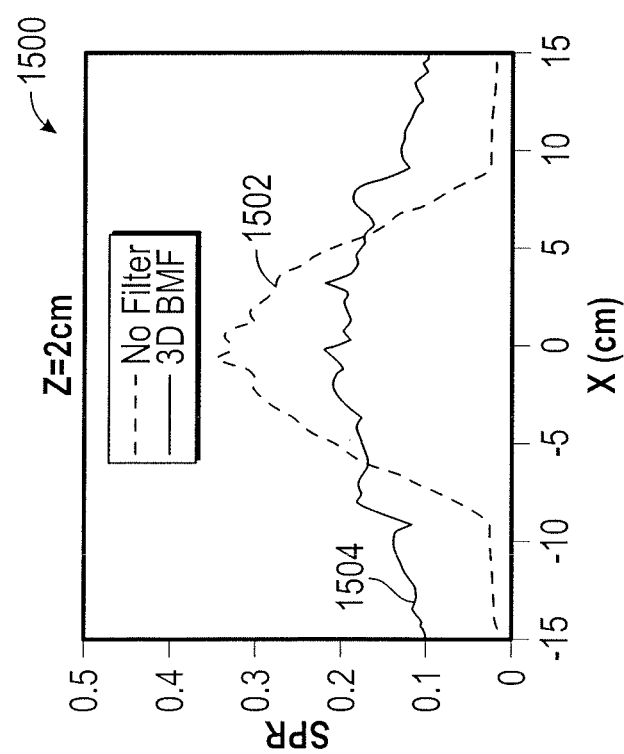
FIG. 15A illustrates comparison of a first line profile (without using a filter) and a second line profile (using a filter) through the simulated SPR maps images along the horizontal dimension shown in FIG. 14A.

FIGS. 15A-15B illustrate comparison of line profiles through the simulated SPR maps. FIG. 15A illustrates comparison 1500 of a line profile 1502 (without using a filter) and a line profile 1504 (using a filter) through the simulated SPR maps along the horizontal dimension 1402 (i.e. z=2 cm from the chest wall) shown in FIG. 14A. FIG. 15B illustrates comparison 1510 of a line profile 1502 (without using a filter) and a line profile 1504 (using a filter) through the simulated SPR map along the vertical dimension 1404 (i.e. midline of the breast) shown in FIG. 14A. FIGS. 15A-15B further demonstrate the reduction in SPR near the posterior, mid-line region of the breast. As provided above, designing a 3D-beam modulation filter that perfectly equalizes the detected signal may not be an optimal choice and this is evident given the increase in SPR near the periphery of the breast, as illustrated in FIG. 15A.

The dose deposited to the radiosensitive tissue within the breast (e.g. fibroglandular tissue) may also be estimated using Monte Carlo simulation techniques. For example the deposited dose estimation may be determined for the V3 phantom at a volumetric glandular fraction of 17% and a 1.5 mm thickness. The reduction in glandular dose after introducing the 3D-beam modulation filter was 34%, 45%, and 40% for the V1, V3, and V5 phantoms, respectively, when the dose was normalized to the number of quanta reaching the detector under the thickest region of the breast. This normalization was used to compare the dose for an equivalent signal-to-noise ratio (SNR) at the detector. The results shown here demonstrate that at a constant SNR the introduction of a 3D-beam modulation filter results in a large reduction in radiation dose delivered to the person. It also demonstrates that at equivalent dose levels the configuration with a 3D-beam modulation filter would have a higher SNR than the configuration without a 3D-beam modulation filter.

As provided above, the present invention uses a large cohort of person bCT volume datasets to design a 3D-beam modulation filter. According to some embodiments, the 3D-beam modulation filter may include a combined wedge and bowtie-shaped filter. A wedge-shaped filter is used to vary the intensity of the x-ray beam in the cone angle direction to compensate for the differential thickness of breast tissue from the posterior 204 to the anterior 206 regions of the breast. A bowtie-shaped filter is used to vary the intensity of the x-ray beam in the fan angle direction to compensate for the differential thickness of breast tissue from the central 214 to the peripheral 216 regions of the breast. The design of the wedge-shaped filter, the bowtie-shaped filter and the combined wedge and bowtie-shaped filter are discussed next.

Design of the Wedge-Shaped Filter

Figure 16:
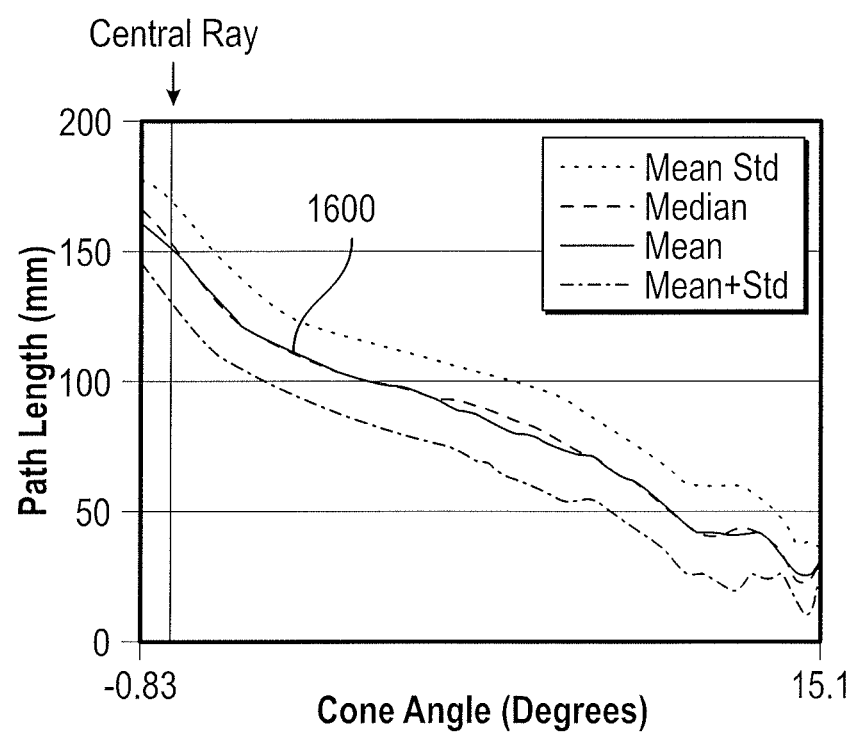
FIG. 16 illustrates cone angle path length profile results combining a breast CT images of a plurality of persons in accordance with embodiments of the invention.

Using the specific geometrical specifications of the bCT scanner of interest (e.g. source to isocenter distance (SIC), source to detector distance (SID), location of the central ray on the detector, etc.), a person's breast image may be used to analytically determine x-ray path length as a function of position along the z-axis of the detector panel (i.e. cone-angle direction). Referring back to FIG. 2A, ray paths in the cone angle direction incident on the detector panel 110 are illustrated. By measuring the x-ray path length as a function of cone angle along the midline z-axis of the detector panel 110 for a single projection, a complete description of the signal attenuation may be determined along the z dimension. This process may be repeated for any number of projections. Results of the combined path length profiles for 215 person images (2 orthogonal views for each case) are shown in FIG. 16 using images acquired on a prototype bCT system. The curve 1600 illustrated in FIG. 16 represents the mean path length traveled by the x-rays through the breast from the chest wall to the nipple in the z-direction. The wedge-shaped filter is designed to compensate for the large difference in path length 1600 illustrated in FIG. 16.

As it would be expected, the person's breast is thickest near the chest wall and tapers off towards the nipple. Depending on the availability of person data sets, any number of images may be combined to determine an "average" path length profile (e.g. the curve 1600 illustrated in FIG. 16) for a given bCT system. The exemplary curve 1600 shown in FIG. 16 takes the average path length profile for all person data sets (i.e. data sets for 215 persons) independent of breast size and shape. According to various embodiments, the path length profiles may be classified by person diameter, volume, and/or any other geometrical constraint resulting in different path length profiles for each person class. For example, the path length profiles illustrated in FIG. 16 may be grouped under 5 different classes such as x-small, small, medium, large and x-large, based on the breast size as discussed previously. A wedge-shaped filter may be formed for each category. Then, for a given person, one of the five wedge-shaped filters may be selected based on the actual breast shape or sizeshape for the person.

The design considerations for the thickness of the wedge-shape filter are discussed next.

Using the exponential attenuation of photons, the photon fluence or exposure (using a photon fluence to exposure conversion factor) at the detector may be determined for each path length within the entire path length profile 1600 illustrated in FIG. 16. In order to equalize the detector signal across the detector panel, the actual detector response in ADUs may be determined. For this purpose, an ionization chamber may be used to measure the exposure at the scanner isocenter (or any location within the x-ray FOV) for any arbitrary x-ray techniques factors (e.g. kVp, filtration). The ADU values may then be measured from the projection image at various locations along the cone and fan angle directions to determine a relationship between the ADU value recorded in the detector and the exposure at the scanner isocenter. By sweeping through all possible tube current values (up to detector saturation), a complete description of the ADU as a function of exposure at the isocenter may be determined for each combination of x-ray technique factors.

Figure 17B:
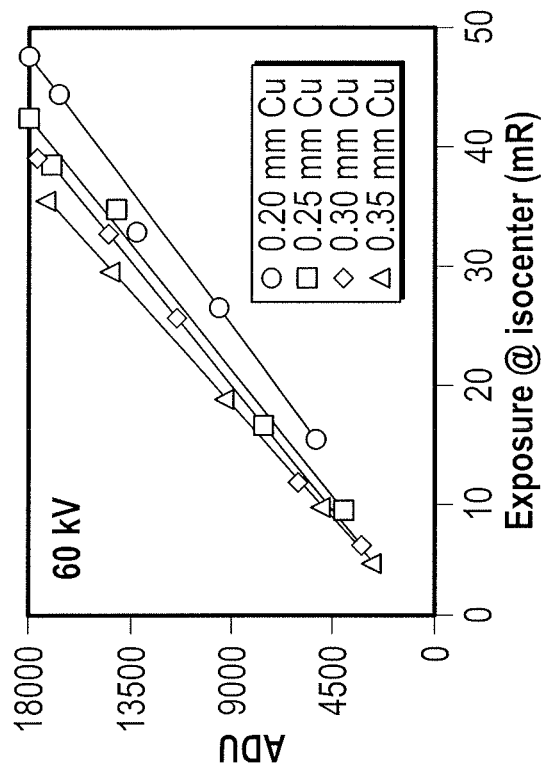
FIG. 17B illustrates the measured ADU (near the location of the central ray on the detection plane) as a function of exposure at the isocenter for the bCT scanner in accordance with embodiments of the invention.
Figure 17A:
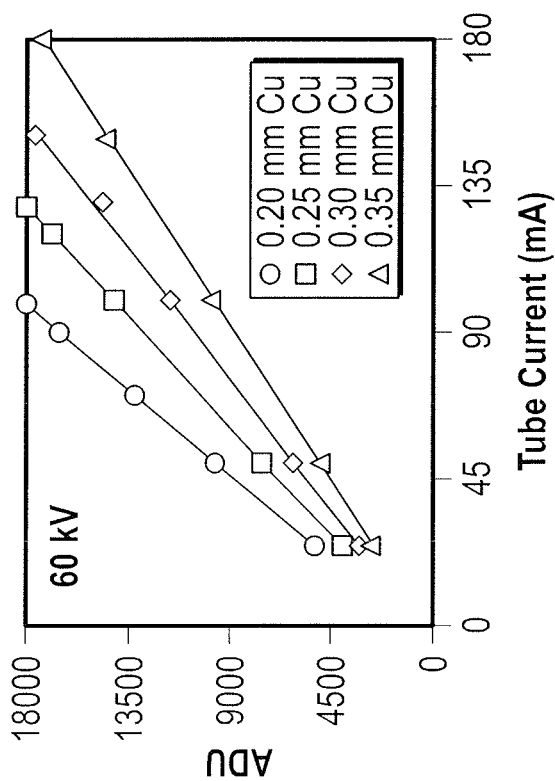
FIG. 17A illustrates the measured ADU (near the location of the central ray on the detection plane) as a function of tube current in accordance with embodiments of the invention.

FIG. 17A illustrates the measured ADU (near the location of the central ray on the detection plane) as a function of tube current. FIG. 17B illustrates the measured ADU (near the location of the central ray on the detection plane) as a function of exposure at the isocenter for the bCT scanner. These specific measurements were made using a 60 kV x-ray beam with increasing thicknesses of copper filtration, measured on a prototype bCT system. The various curves illustrate differences in x-ray tube (e.g. x-ray source) output related to the amount of added copper filtration.

A tungsten anode spectral model may be used to compute the polyenergetic x-ray spectrum for a selected kV/filter combination. Monotonically increasing thickness of a breast tissue of any given composition may then be used to mathematically filter the computed x-ray spectrum. Making use of a photon fluence to exposure conversion factor, the exposure as a function of x-ray attenuation through the breast tissue may then be calculated. Using these data, and the aforementioned data relating ADU values to exposure measurements, the ADU may be determined as a function of path length through the breast for a selected kV/filter combination.

To equalize the ADU values along the cone angle direction of the detector, the ADU value resulting from the x-ray path traversing through the thickest region of the detector (in the cone angle direction) may be used as the normalization value ($ADU_0$) since this is the location at which the maximum amount of incident photons is necessary to achieve an optimal signal-to-noise ratio while simultaneously keeping the dose as low as two-view mammography.

Equalization of the ADU value may be accomplished by an algorithm to determine the thickness of a given filter material (e.g. aluminum, copper, titanium) that is needed to compensate for the decrease in path length relative to $ADU_0$ as a function of position along the cone angle direction of the detector.

Figure 18A:
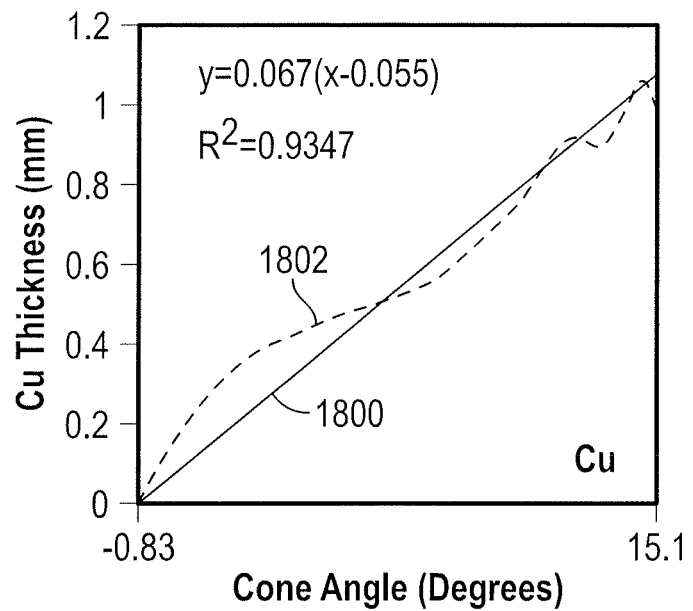
FIG. 18A illustrates the computed filter thickness for an exemplary copper wedge-shaped filter as a function of cone angle (data points) and a linear regression fit (solid line) in accordance with embodiments of the invention.
Figure 18B:
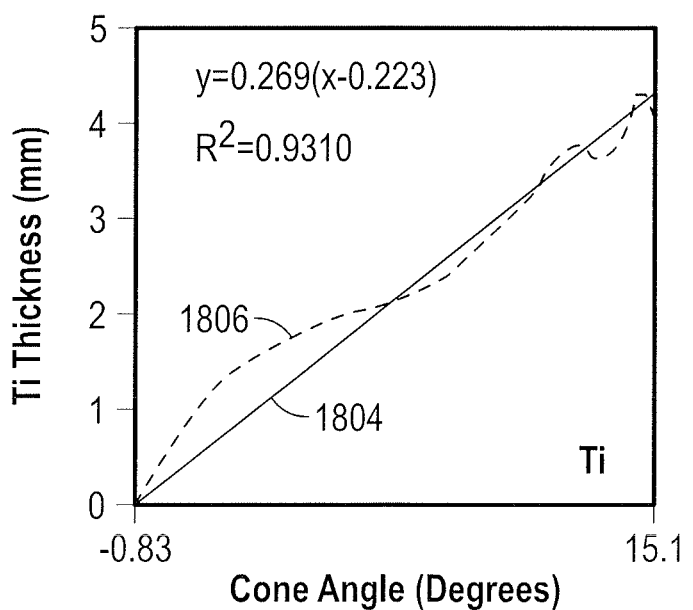
FIG. 18B illustrates the computed filter thickness for an exemplary titanium wedge-shaped filter as a function of cone angle (data points) and a linear regression fit (solid line) in accordance with embodiments of the invention.
Figure 18C:
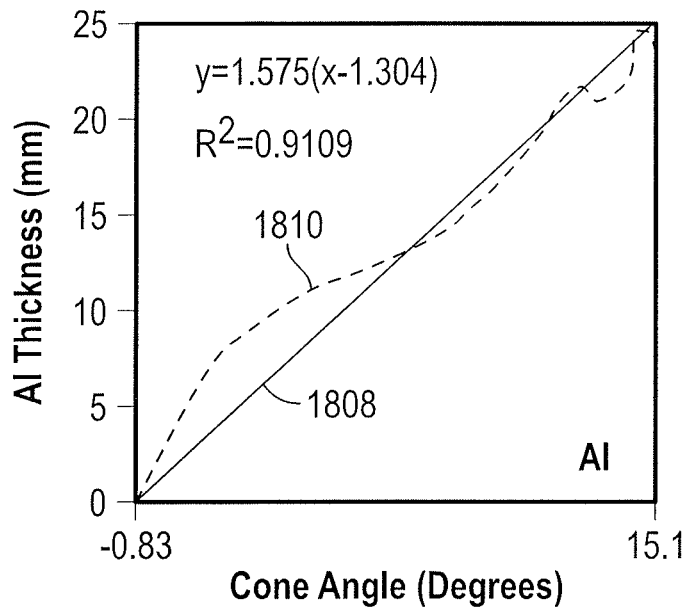
FIG. 18C illustrates the computed filter thickness for an exemplary aluminum wedge-shaped filter as a function of cone angle (data points) and a linear regression fit (solid line) in accordance with embodiments of the invention.

FIGS. 18A-18C illustrate the thickness of the wedge-shape filter designed based on the data illustrated in FIG. 16 as a function of the material of the filter. The x-axis of FIGS. 16 and 18A-18C represent the cone angle in degrees. A cone angle of 0 degrees corresponds to location of the central ray.

Specifically, FIG. 18A illustrates the computed filter thickness for copper wedge-shaped filter as a function of cone angle (dashed line) 1802 and a linear regression fit (solid line) 1800. FIG. 18B illustrates the computed filter thickness for titanium wedge-shaped filter as a function of cone angle (dashed line) 1806 and a linear regression fit (solid line) 1804. The titanium wedge-shaped filter requires a thicker amount of material because of the relatively lower atomic number (Z=22) compared to copper (Z=29). FIG. 18C illustrates the computed filter thickness for aluminum wedge-shaped filter as a function of cone angle (dashed line) 1808 and a linear regression fit (solid line) 1810. Aluminum (Z=13) attenuates the radiation significantly less than copper and titanium for the same reasons noted above.

Figure 19A:
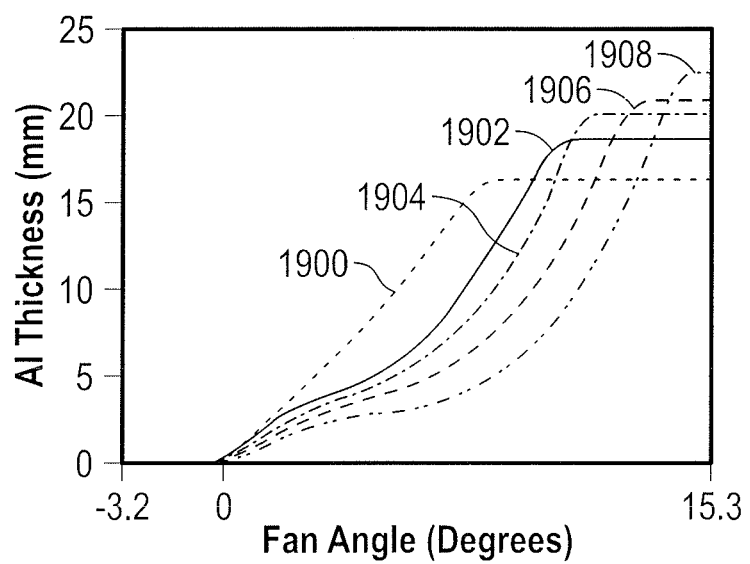
FIG. 19A illustrates the thickness profile in the z-direction of an exemplary aluminum wedge-shaped filter for each breast class in accordance with embodiments of the invention.
Figure 19B:
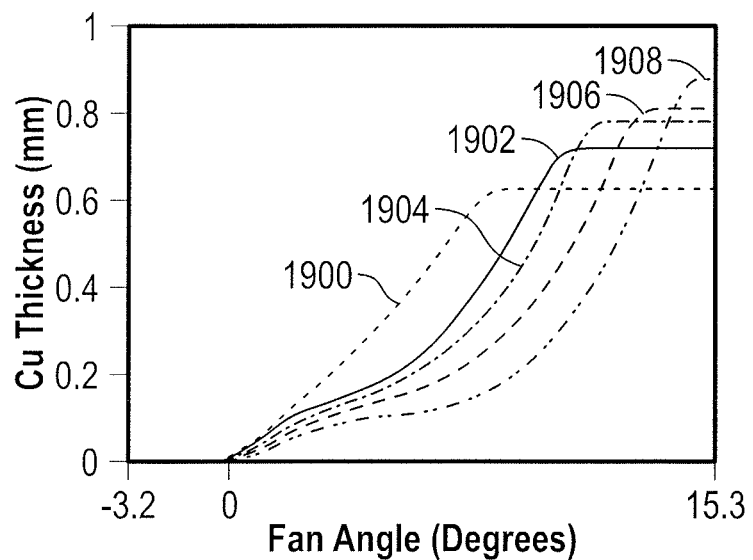
FIG. 19B illustrates the thickness profile in the z-direction of an exemplary copper wedge-shaped filter for each breast class in accordance with embodiments of the invention.
Figure 19C:
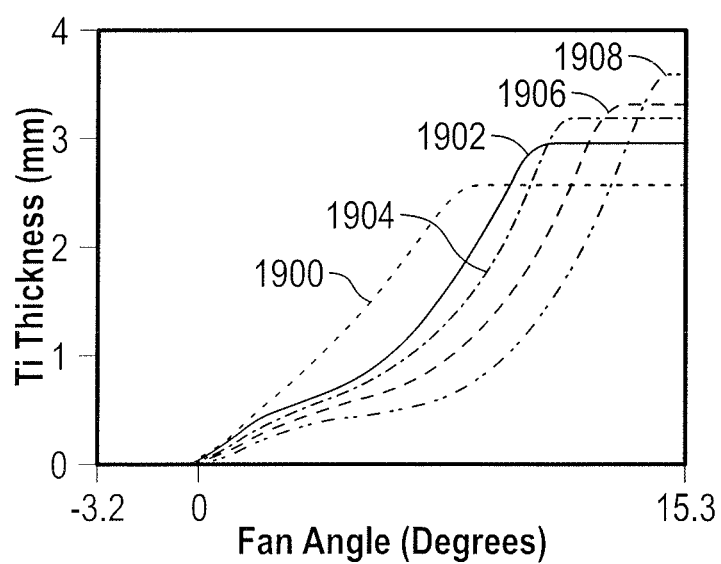
FIG. 19C illustrates the thickness profile in the z-direction of an exemplary titanium wedge-shaped filter for each breast class in accordance with embodiments of the invention.

FIGS. 19A-19C illustrates wedge-shaped filter designs (i.e. the thickness profiles in the z-direction) 1900, 1902, 1904, 1906, 1908 for each breast class (e.g. V1, V2, V3, V4 and V5). FIG. 19A illustrates the thickness profile in the z-direction of an exemplary aluminum wedge-shaped filter for each breast class V1, V2, V3, V4 and V5. FIG. 19B illustrates the thickness profile in the z-direction of an exemplary copper wedge-shaped filter for each breast class V1, V2, V3, V4 and V5. FIG. 19C illustrates the thickness profile in the z-direction of an exemplary titanium wedge-shaped filter for each breast class V1, V2, V3, V4 and V5. As it may be seen by comparing curves 1900-1908 on each one of FIG. 19A, FIG. 19B and FIG. 19C, a wedge-shaped filter made of aluminum has a much larger thickness (e.g. about 7 to 25 times larger) than wedge-shaped filters made of copper or titanium. An ideal filter should be thin enough so that it fits into the geometrical constraints of the particular system, but the filter should also be thick enough that it may be machined to a desired shape and form. Additional metrics that are important to consider when designing a modulation filter may include, for example, differences in scattered radiation levels and beam hardening of the x-ray beam as the x-ray beam traverses the modulation filter.

Design of the Bowtie-Shaped Filter

Using the same framework as the design of the wedge-shaped filter, a person's breast image may be used to simulate the x-ray path length as a function of position along the x-axis of the detector panel (i.e. fan-angle direction) to determine the design of the bowtie-shaped filter. This process may be repeated for any number of cone angles from the posterior to anterior limits of the detector panel.

Figure 20:
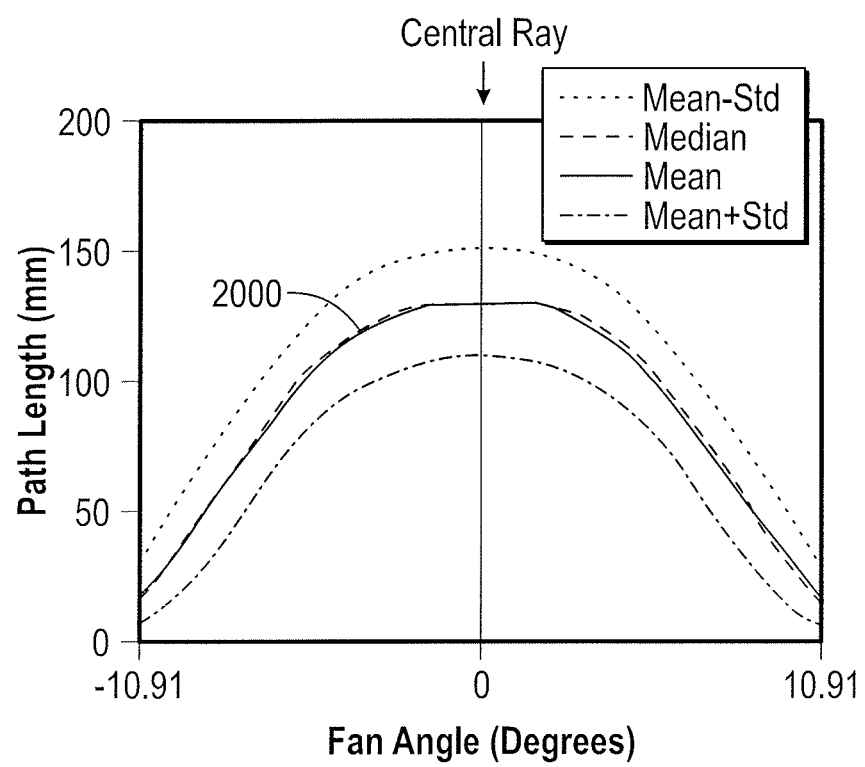
FIG. 20 illustrates fan angle path length profile results combining breast CT images from a plurality of persons in accordance with embodiments of the invention.

Referring back to FIG. 2B, ray paths in the fan angle direction incident on the anterior edge of the detector panel 110 are shown. By measuring the x-ray path length as a function of fan angle along the entire detector panel 110, a complete description of the signal attenuation may be determined. This process may be repeated for any number of views. Results of the combined path length profiles for 215 person images (2 orthogonal views for each case) are shown in FIG. 20 using images acquired on a prototype bCT system. The curve 2000 illustrated in FIG. 20 represents the pathway traveled by the x-rays through the breast from superior part to inferior part of the breast in the x-direction. The bowtie-shaped filter is designed to compensate to the pathway illustrated in FIG. 20.

The fan angle path length profiles become much narrower as the cone angle increases towards the anterior part of the breast CT images. This effect in the cone angle direction is accounted for in the wedge-shaped filter design. Therefore, the fan angle path length profiles at a cone angle of 0° are used in the present invention. This process may be repeated for any number of projections within the 360° motion of the bCT gantry. The example shown in FIG. 20 takes the average fan-angle path length profile for all person data sets (e.g. 215 person images, 2 orthogonal projections for each image) independent of breast size and shape.

The design considerations for the thickness of the wedge-shape filter are discussed next.

Figure 21A:
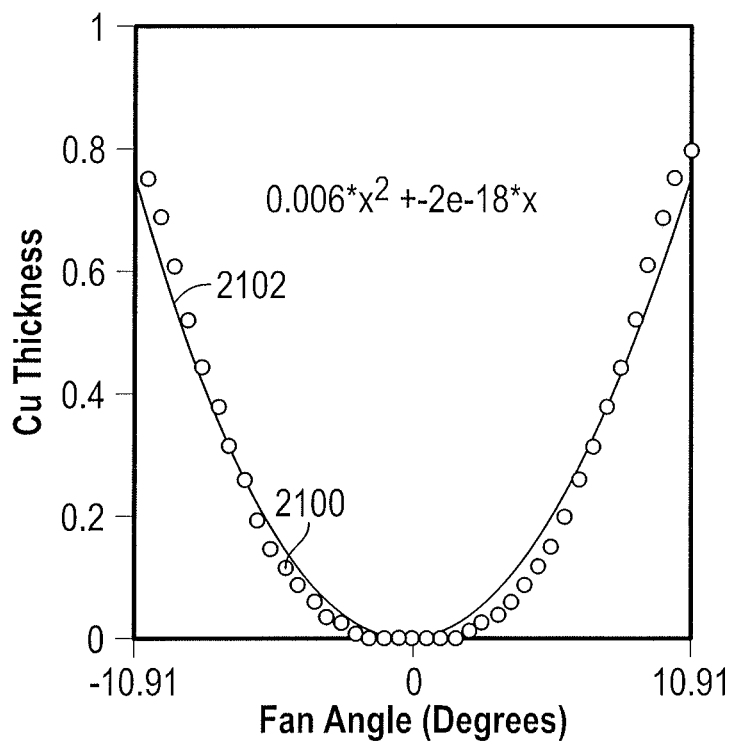
FIG. 21A illustrates the computed filter thickness for an exemplary copper bowtie-shaped filter as a function of cone angle (data points) and a linear regression fit (solid line) in accordance with embodiments of the invention.
Figure 21B:
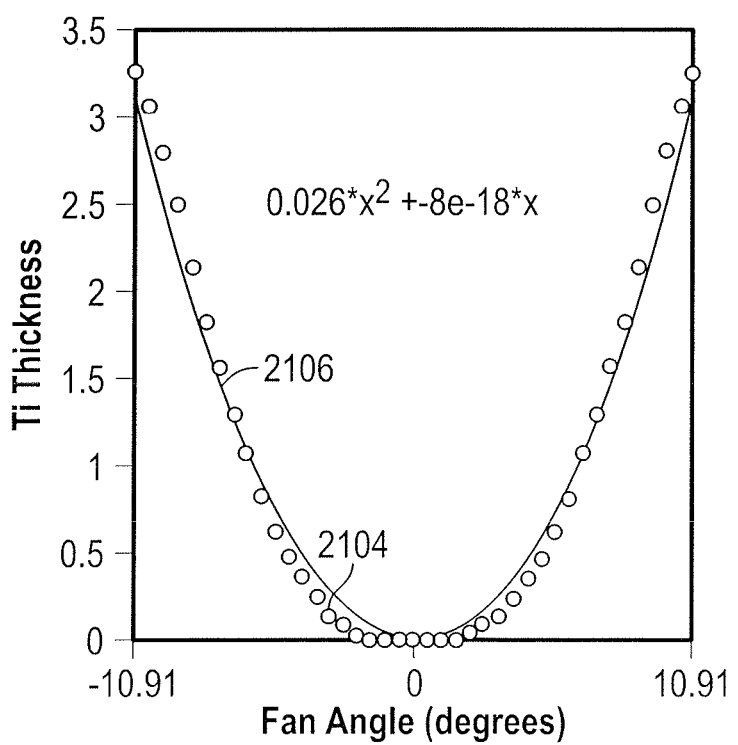
FIG. 21B illustrates the computed filter thickness for an exemplary titanium bowtie-shaped filter as a function of cone angle (data points) and a linear regression fit (solid line) in accordance with embodiments of the invention.
Figure 21C:
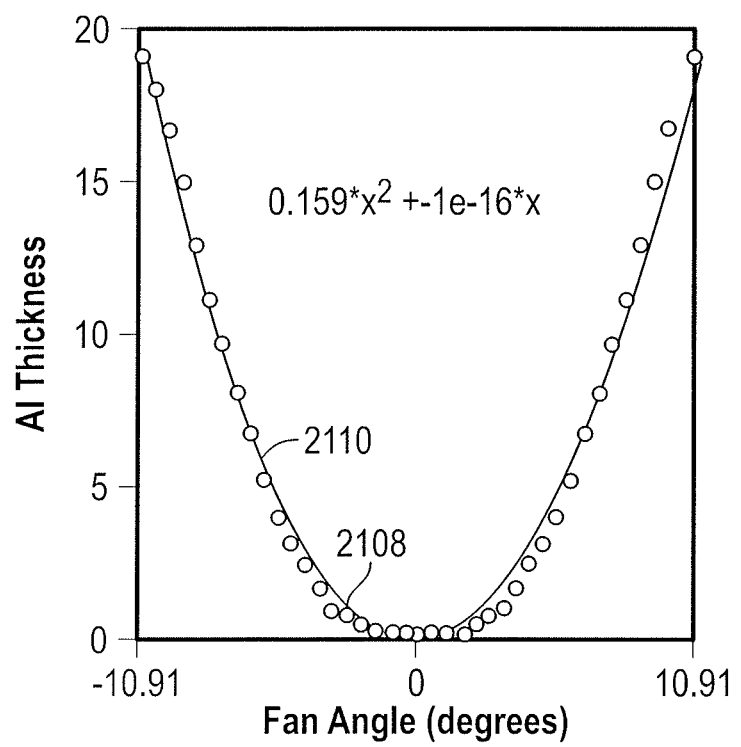
FIG. 21C illustrates the computed filter thickness for an exemplary aluminum bowtie-shaped filter as a function of cone angle (data points) and a linear regression fit (solid line) in accordance with embodiments of the invention.

FIGS. 21A-21C illustrate the thickness of the bowtie-shaped filter designed based on the data illustrated in FIG. 20 as a function of the material of the filter. The x-axis of FIGS. 20 and 21A-21C represent the fan angle in degrees.

FIG. 21A illustrates the computed filter thickness for copper bowtie-shaped filter as a function of fan angle (data points) 2100 and a parabolic fit (solid line) 2102. Copper greatly attenuates the radiation. As a result, a thin bowtie-shaped filter may be formed using copper. FIG. 21B illustrates the computed filter thickness for the titanium bowtie-shaped filter as a function of cone angle (data points) 2104 and a linear regression fit (solid line) 2106. Titanium attenuates the radiation slightly less than copper. Thus, a titanium bowtie-shaped filter needs to be slightly thicker than a copper bowtie-shaped filter to achieve the same filtering results. FIG. 21C illustrates the computed filter thickness for aluminum bowtie-shaped filter as a function of cone angle (data points) 2108 and a linear regression fit (solid line) 2110. Aluminum attenuates the radiation significantly less than copper and titanium as discussed previously.

Figure 22A:
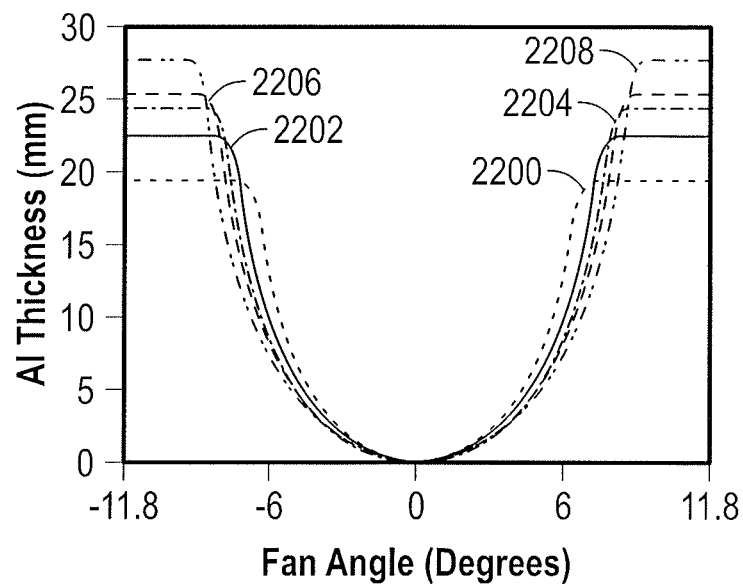
FIG. 22A illustrates the thickness profile in the x-direction of an exemplary aluminum bowtie-shaped filter for each breast class in accordance with embodiments of the invention.
Figure 22B:
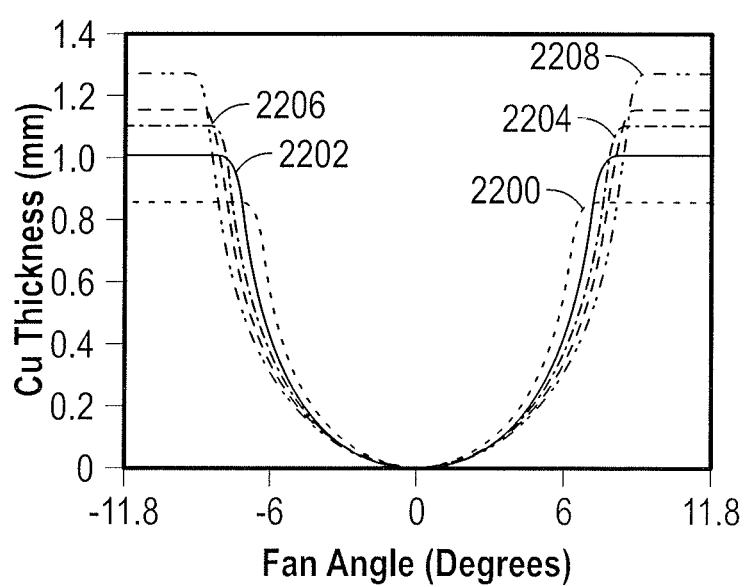
FIG. 22B illustrates the thickness profile in the x-direction of an exemplary copper bowtie-shaped filter for each breast class in accordance with embodiments of the invention.
Figure 22C:
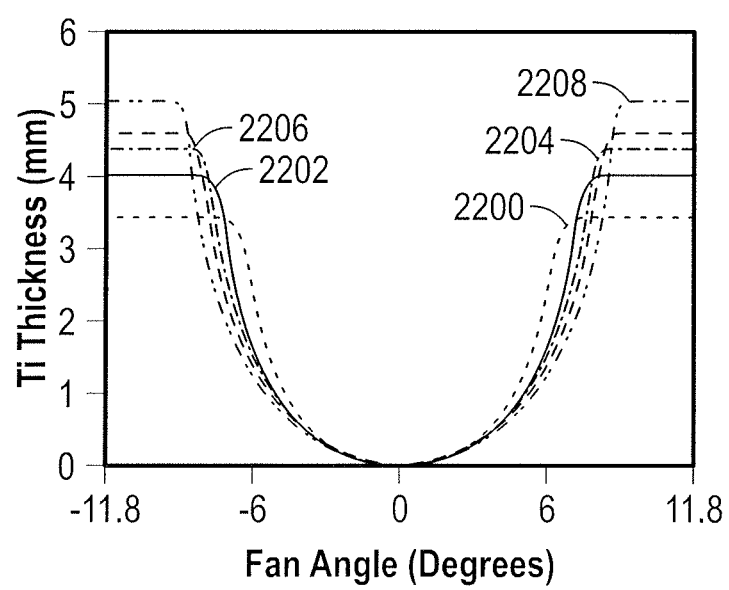
FIG. 22C illustrates the thickness profile in the x-direction of an exemplary titanium bowtie-shaped filter for each breast class in accordance with embodiments of the invention.

FIGS. 22A-22C illustrates bowtie-shaped filter designs (i.e. the thickness profiles in the x-direction) 2200, 2202, 2204, 2206 and 2208 for each breast class (e.g. V1, V2, V3, V4 and V5, respectively). FIG. 22A illustrates the thickness profile in the x-direction of an exemplary aluminum bowtie-shaped filter for each breast class V1, V2, V3, V4 and V5. FIG. 22B illustrates the thickness profile in the x-direction of an exemplary copper bowtie-shaped filter for each breast class V1, V2, V3, V4 and V5. FIG. 22C illustrates the thickness profile in the x-direction of an exemplary titanium bowtie-shaped filter for each breast class V1, V2, V3, V4 and V5. As it may be seen by comparing curves 2200-2208 on each one of FIG. 22A, FIG. 22B and FIG. 22C, a bowtie-shaped filter made of aluminum has a much larger thickness (e.g. about 5 to 15 times larger) than bowtie-shaped filters made of copper or titanium. Accordingly, copper and titanium nay be a better choice of material for the bowtie-shaped filter.

Design of Combined Wedge-Shaped and Bowtie-Shaped Filter

Figure 23:
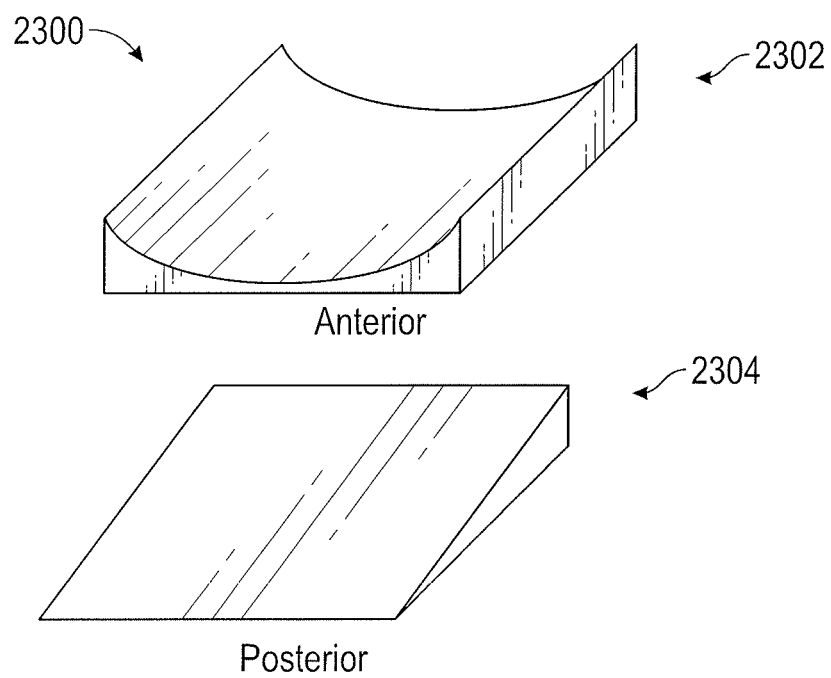
FIG. 23 is a diagram of combining an exemplary bowtie-shaped filter and an exemplary wedge-shaped filter used in tandem in accordance with embodiments of the invention.

The present invention describes a method for designing a combined wedge-shaped and bowtie-shaped filter for equalizing the signal at the detector panel in both the cone angle (i.e. vertical) and fan angle (i.e. horizontal) directions of the detector panel. FIGS. 18A-18C and 21A-21C illustrate an exemplary one-dimensional design shapes for a wedge-shaped filter and a bowtie-shaped filter, respectively. These shapes may be fit to polynomial functions (or other mathematical functions) and then used in tandem to compute the overall shape of a single 3D-beam modulation filter. FIG. 23 is a diagram of combining a bowtie-shaped filter 2302 and a wedge-shaped filter 2304 used in tandem. According to various embodiments, the bowtie-shaped filter 2302 may be provided adjacent to the wedge-shaped filter 2304 to form the combined bowtie-shaped and wedge-shaped filter 2300 illustrated in FIG. 23.

Figure 24A:
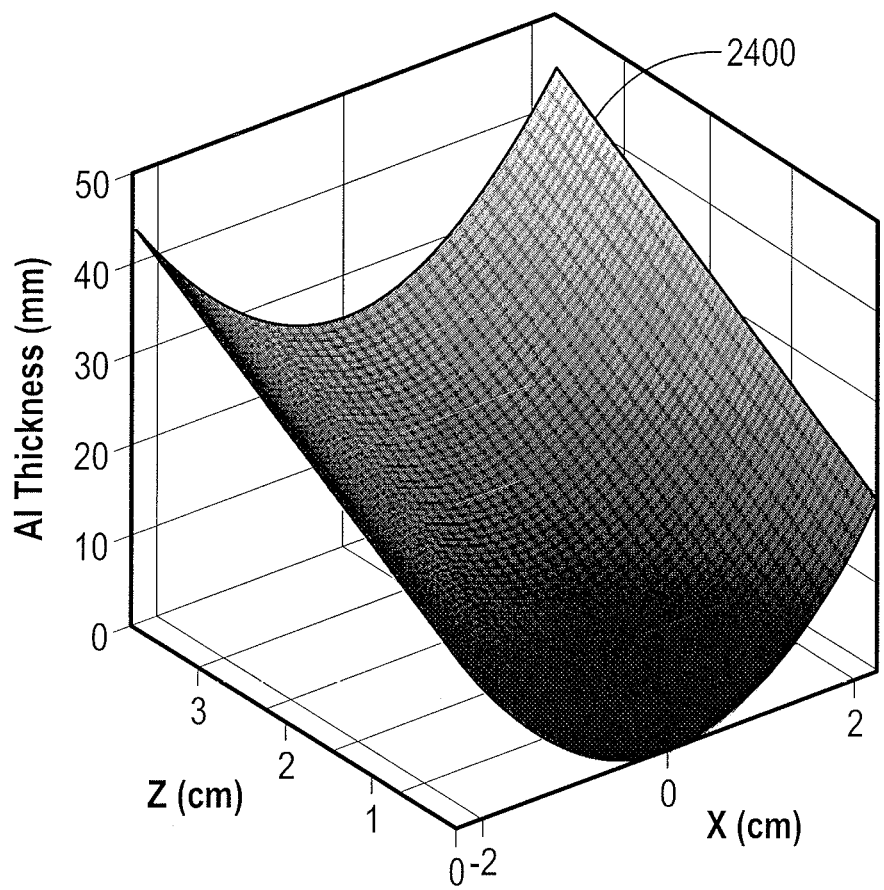
FIG. 24A illustrates the 3D shape of an aluminum combined bowtie-shaped and wedge-shaped filter using a surface plot of the aluminum combined filter thickness profile in the z-direction and x-direction in accordance with embodiments of the invention.
Figure 24B:
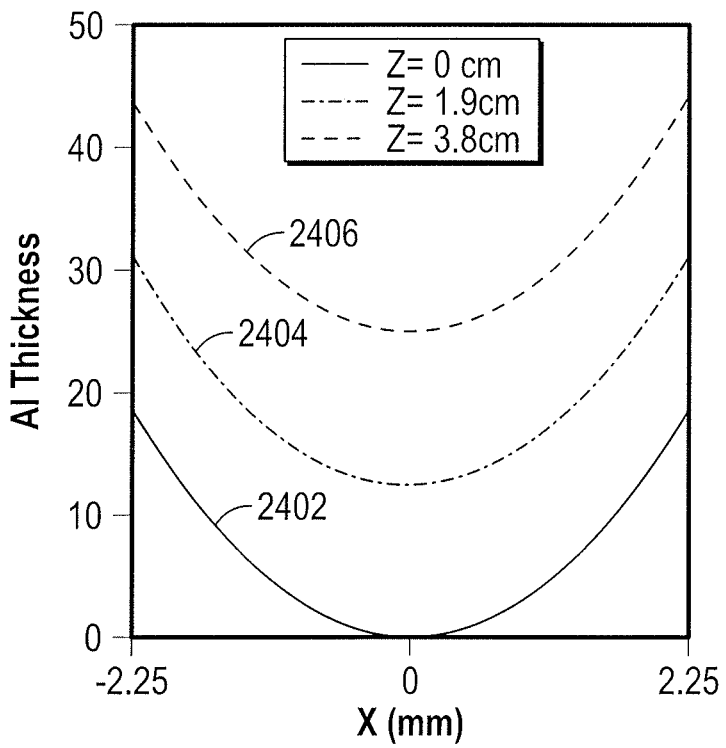
FIG. 24B illustrates characteristics of an aluminum combined bowtie-shaped and wedge-shaped filter using lines profiles at various z-locations in accordance with embodiments of the invention.
Figure 24C:
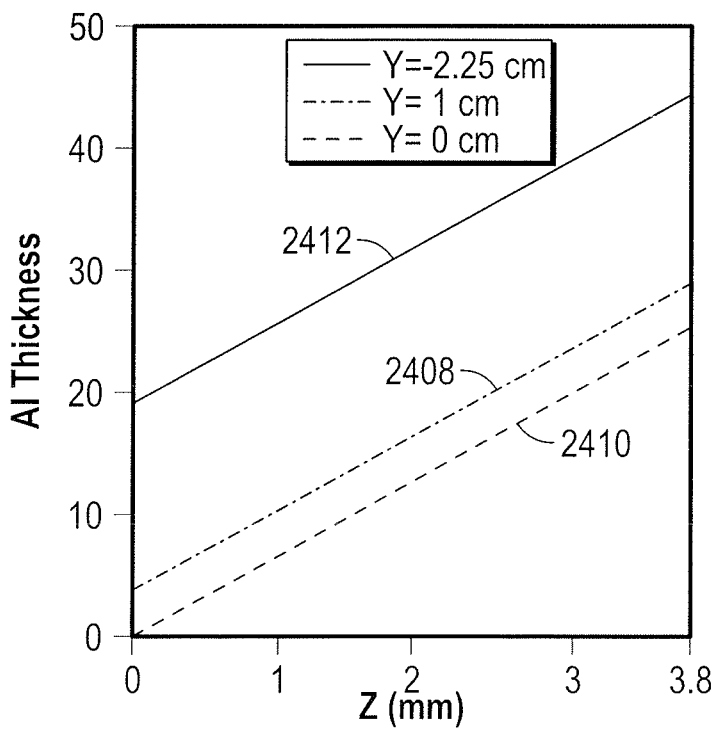
FIG. 24C illustrates characteristics of an aluminum combined bowtie-shaped and wedge-shaped filter using lines profiles at various x-locations in accordance with embodiments of the invention.

FIGS. 24A-24C illustrate 3D shape of an aluminum combined bowtie-shaped and wedge-shaped filter. FIG. 24A illustrates a surface plot 2400 of the aluminum combined filter thickness profile in the z-direction (i.e. cone angle direction) and x-direction (i.e. fan angle direction). FIG. 24B illustrates line profile 2402 corresponding at z=0 cm, line profile 2404 corresponding at z=1.9 cm, line profile 2406 corresponding at z=3.8 cm. FIG. 24C illustrates line profile 2408 corresponding at y=0 cm, line profile 2410 corresponding at y=1.0 cm, line profile 2412 corresponding at y=−2.25 cm.

Figure 25:
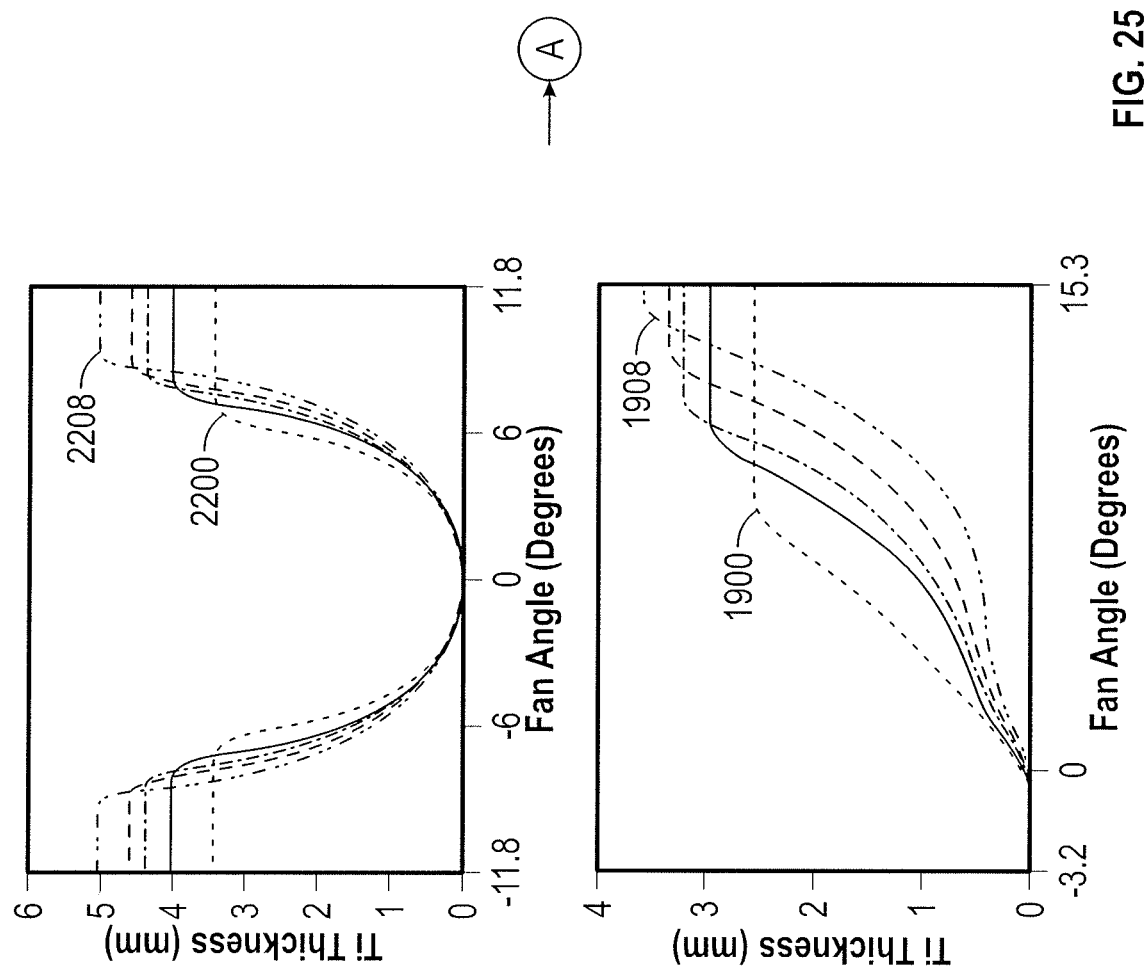
FIG. 25 illustrates the combined filter shape of titanium 3D-beam modulation filter for the first profile (e.g. V1, the x-small size breast) and the combined filter shape of titanium 3D-beam modulation filter for the fifth profile (e.g. V5, the x-large size breast).
Figure 25:
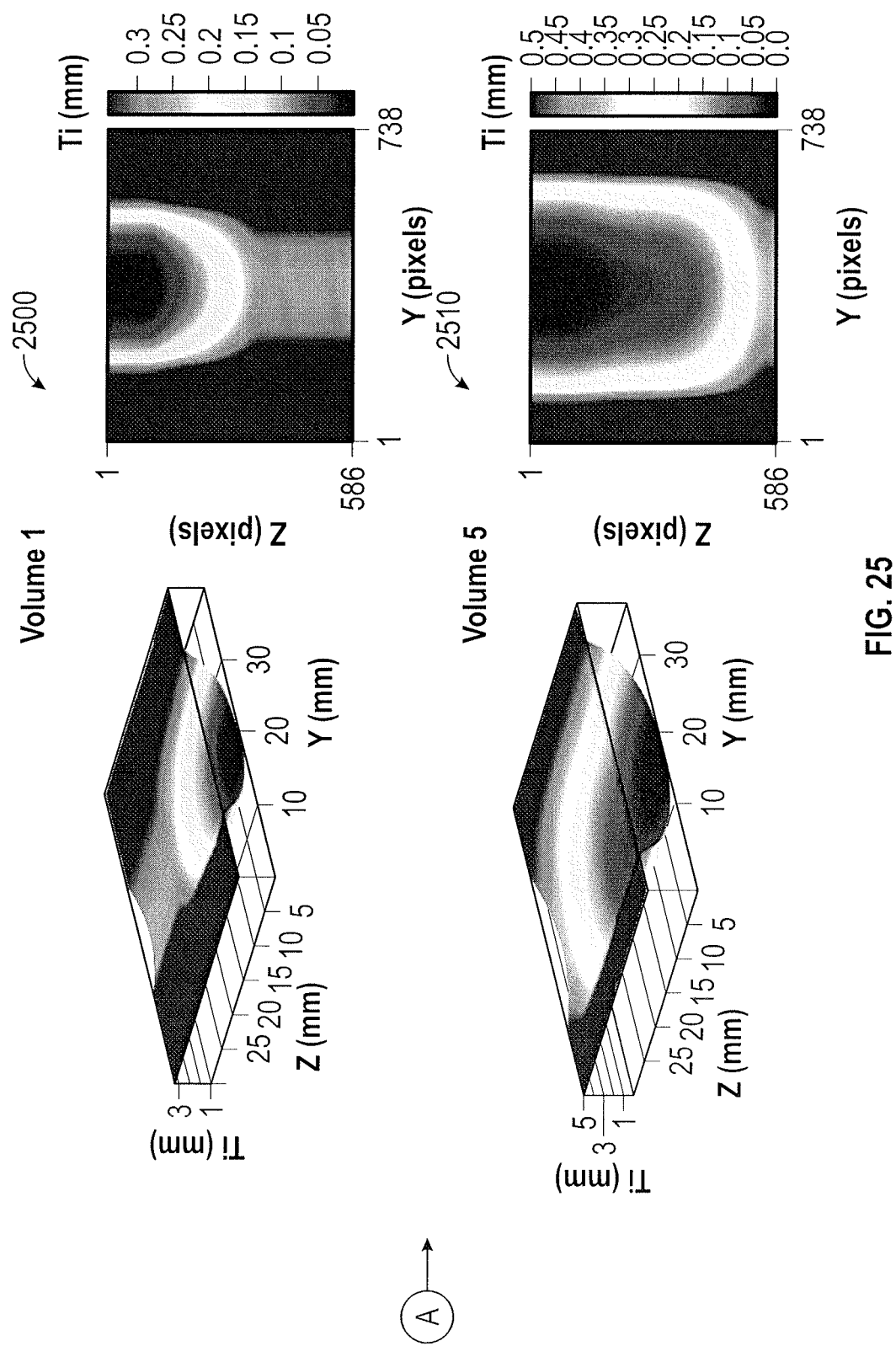

Once the plurality of wedge-shaped filters and the bowtie-shaped filters are determined as illustrated in FIGS. 19A-19C and 22A-22C, respectively, the wedge-shaped filter and the bowtie-shaped filter corresponding to each profile (e.g. V1, V2, V3, V4 and V5) may be combined to form the combined filter for each profile. FIG. 25 illustrates the combined filter shape 2500 of titanium 3D-beam modulation filter for the first profile (e.g. V1, the x-small size breast) and the combined filter shape 2510 of titanium of titanium 3D-beam modulation filter for the fifth profile (e.g. V5, the x-large size breast). The combined filter shape 2500 of titanium 3D-beam modulation filter for the first profile (e.g. V1, the x-small size breast) is obtained by combining the bowtie-shaped filter design 2200 for V1 and the wedge-shaped filter design 1900 for V1. The combined filter shape 2510 of titanium 3D-beam modulation filter for the fifth profile (e.g. V5, the x-large size breast) is obtained by combining the bowtie-shaped filter design 2208 for V5 and the wedge-shaped filter design 1908 for V5.

The introduction of the combined filter results in a reduction in the radiation dose delivered to the person while not having a negative impact on the image quality. For example, using the combined filter shape 2510, the reduction in the radiation dose on the small size breast corresponding to breast class V1 is about 33%, the reduction in the radiation dose on the medium size breast corresponding to breast class V3 is about 47%, and the reduction in the radiation dose on the large size breast corresponding to breast class V5 is about 54%.

Exemplary Method

Embodiments provide a plurality of 3D-beam modulation filters for a variety of breast shapes. A best fitting 3D-beam modulation filter may be selected for a given person based on the actual shape of the person's breast. For example, the breast of the person may be examined by a technician and a corresponding pre-determined breast class (e.g. one of V1, V2, V3, V4 or V5 discussed above) may be identified. According to various embodiments, the breast of the person may be evaluated using a laser evaluating system to determine a pre-determined breast class that best fits the person's breast.

When the person is associated with one of the profiles, a breast immobilizer associated with the person's identified profile may be used during the imaging process to ensure that the breast is centered in the field of view of the scanner. A 3D-beam modulation filter corresponding to the identified profile may be used for generating CT images of person's breast. The use of the combined breast immobilizer and 3D-beam modulation filter corresponding to the specific shape of the person's breast enables reduction of the radiation dose on the person without compromising the image quality.

Figure 26:
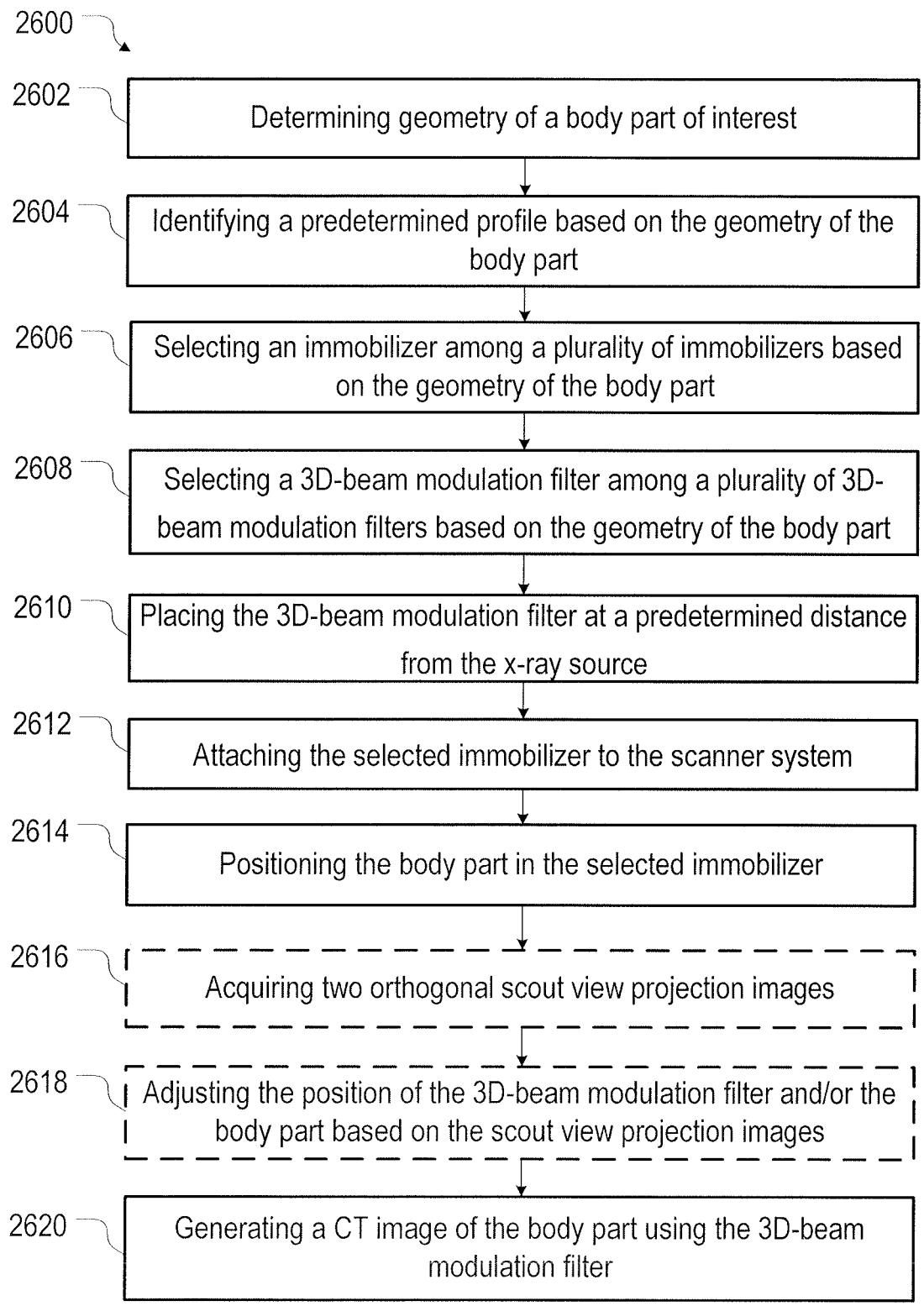
FIG. 26 illustrates a flowchart of steps for generating a CT image of a body part using a selected 3D-beam modulation filter in accordance with embodiments of the invention.

FIG. 26 illustrates a flowchart 2600 of steps for generating a CT image of a body part using a size or shape specific 3D-beam modulation filter. At step 2602, an actual shape or size of a body part of interest (e.g. breast of a person) may be determined. According to various embodiments, the actual shape or size of the body part may be determined by visual inspection of a person (e.g. x-ray technician) or using a laser-based evaluation system. In some embodiments, determining the shape or size of the body part may include identifying a predetermined profile based on the shape or size of the body part (step 2604). That is, determining the shape or size of the body part may include determining if the body part is similar in shape and/or size to one of the plurality of predetermined profiles.

At step 2606, an immobilizer (e.g. an immobilizing mold or a confining mask) may be selected among a plurality of immobilizers based on the determined shape or size of the body part or the identified predetermined profile. The selected immobilizer may conform to the body part to be imaged (e.g. the breast) and may place the body part in the field of view of the scanner system. In some embodiments, an immobilizer may be formed for each one of the plurality of predetermined profiles.

At step 2608, a 3D-beam modulation filter may be selected among a plurality of 3D-beam modulation filters based on the determined shape or size of the body part or the identified predetermined profile. The selected 3D-beam modulation filter may reduce the radiation dose delivered to the body part without compromising on the image quality. In some embodiments, a 3D-beam modulation filter may be formed for each one of the plurality of predetermined profiles.

In some embodiments, the 3D-beam modulation filter may include a combined bowtie-shaped and wedge-shaped filter. Accordingly, a bowtie-shaped filter may be selected among a plurality of bowtie-shaped filters based on the shape or size of the body part or the identified predetermined profile. Similarly, a wedge-shaped filter may be selected among a plurality of wedge-shaped filters based on the shape or size of the body part or the identified predetermined profile. The selected bowtie-shaped filter and the selected wedge-shaped filter may be combined into a combined filter.

At step 2610, the 3D-beam modulation filter may be placed at a predetermined distance from an x-ray source of the body scanner system such that the 3D-beam modulation filter is positioned between the x-ray source and the body part being imaged.

At step 2612, the selected immobilizer may be attached to the scanner system. For example, the immobilizer may be attached to a tabletop of the scanner system using one or more of attachment elements. A first end of the attachment element may be attached to the table top and a second end, opposite from the first end, of the attachment element may be attached to the immobilizer. The body part to be imaged may be placed in the selected immobilizer (step 2614).

If necessary, the position of the 3D-beam modulation filter may be adjusted to account for variation in the positioning of the body part in the x-ray field of view of the scanner system. Assessment of the positioning of the body part and the 3D-beam modulation filter could be accomplished by acquiring two orthogonal (i.e. 90 degrees separated) "scout view" projection images at a low dose level prior to the bCT image acquisition (step 2616). These scout views could then be used to either adjust the position of the 3D-beam modulation filter using a motorized positioning system (e.g. filter positioning system 316 illustrated in FIG. 3) and/or the body part could be adjusted in the FOV by the x-ray technician or by the person themselves (step 2618).

At 2620, a CT image of the body part may be generated using the 3D-beam modulation filter to reduce a radiation dose of the body part.

The various participants and elements shown in FIGS. 1-26 may operate one or more computer apparatuses (e.g., a server computer) to facilitate the functions described herein. Any of the elements in FIGS. 1-26 may use any suitable number of subsystems to facilitate the functions described herein. Examples of such subsystems or components are shown in FIG. 27.

Figure 27:
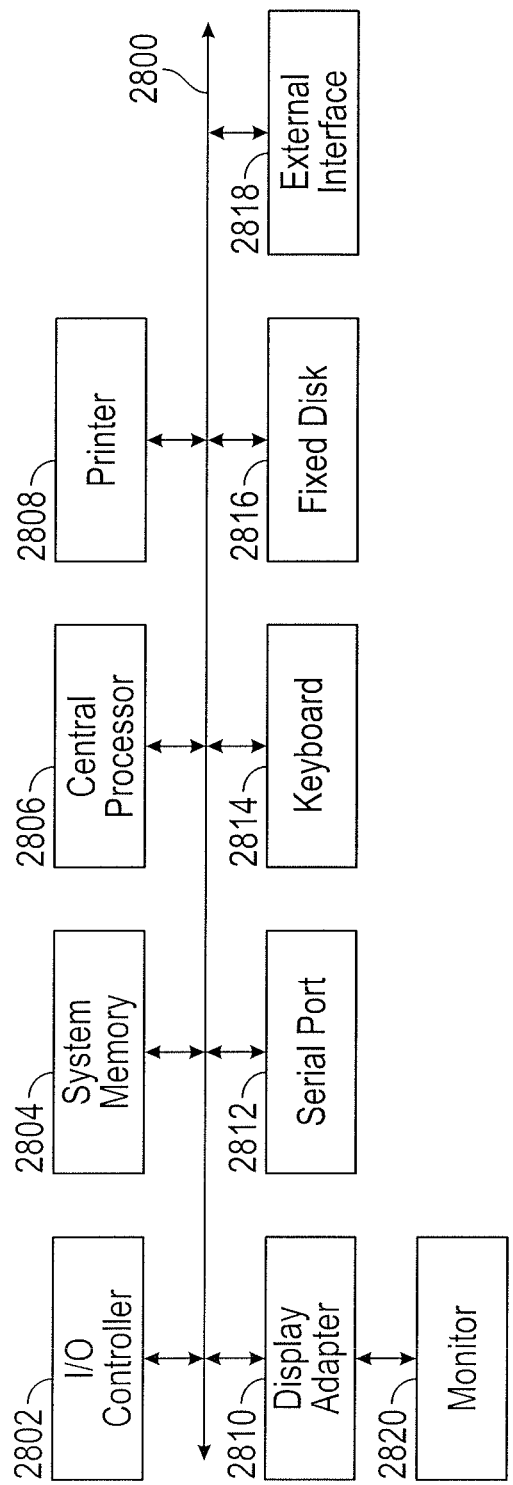
FIG. 27 illustrates shows an exemplary computer system, in accordance with embodiments of the present invention.

The subsystems shown in FIG. 27 are interconnected via a system bus 2800. The subsystems such as a printer 2808, keyboard 2814, fixed disk 2816 (or other memory comprising computer-readable media), monitor 2820, which is coupled to a display adapter 2810, and others are shown. Peripherals and input/output (I/O) devices, which couple to I/O controller 2802, may be connected to the computer system by any number of means known in the art, such as serial port 2812. For example, serial port 2812 or external interface 2818 may be used to connect the computer apparatus to a wide area network such as the Internet, a mouse input device, or a scanner. The interconnection via system bus allows the central processor 2806 to communicate with each subsystem and to control the execution of instructions from system memory 2804 or the fixed disk 2816, as well as the exchange of information between subsystems. The system memory 2804 and/or the fixed disk 2816 may embody computer-readable medium.

Specific details regarding some of the above-described aspects are provided below. The specific details of the specific aspects may be combined in any suitable manner without departing from the spirit and scope of embodiments of the invention.

Storage media and computer readable media for containing code, or portions of code, may include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, data signals, data transmissions, or any other medium which may be used to store or transmit the desired information and which may be accessed by the computer. Based on the disclosure and teachings provided herein, a person of ordinary skill in the art may appreciate other ways and/or methods to implement the various embodiments.

It may be understood that the present invention as described above may be implemented in the form of control logic using computer software in a modular or integrated manner. Based on the disclosure and teachings provided herein, a person of ordinary skill in the art may know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention may become apparent to those skilled in the art upon review of the disclosure. The scope of the invention may, therefore, be determined not with reference to the above description, but instead may be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A method for acquiring a computed tomography (CT) image of a person's breast using a scanner system comprising:
   from a plurality of CT data sets of a plurality of persons, defining a plurality of different breast volume classes, each breast volume class corresponding to a different range of breast volume percentile groups;
   based on at least one of a shape and a size of the person's breast, assigning the person's breast to a breast volume class;
   from a plurality of immobilizers each corresponding to a different breast volume class, selecting an immobilizer corresponding to the breast volume class assigned to the person's breast;
   from a plurality of 3D-beam modulation filters each corresponding to a different breast volume class, selecting a 3D-beam modulation filter corresponding to the breast volume class assigned to the person's breast;
   coupling the selected immobilizer to the scanner system;
   positioning the person's breast in the selected immobilizer; and
   acquiring a computed tomography (CT) image of the person's breast using the scanner system with the selected 3D-beam modulation filter and the selected immobilizer,
   wherein each 3D-beam modulation filter has a three-dimensional shape corresponding to at least one of a size and a three-dimensional shape of one of said breast volume classes so as to equalize intensities of individual x-rays within an x-ray beam after said x-ray beam passes through said person's breast.

2. The method of claim 1, wherein the selected 3D-beam modulation filter is configured to reduce a dose of radiation toward anterior and peripheral regions of the person's breast based on at least one of a shape and a size of the breast volume class assigned to the person's breast.

3. The method of claim 1, wherein acquiring the CT image of the person's breast further comprises:
   collecting x-rays beams emitted from an x-ray source of the scanner system on a detector panel of the scanner system, wherein the x-ray beams emitted by the x-ray source are filtered by the selected 3D-beam modulation filter prior to traveling through the person's breast.

4. The method of claim 1, further comprising:
based on at least one of the shape and the size of the person's breast in addition to the assigned breast volume class, dynamically adjusting a position of the selected 3D-beam modulation filter between the person's breast and an x-ray source of the scanner system, prior to acquiring the computed tomography (CT) image of the person's breast.

5. The method of claim 1, further comprising:
identifying a predetermined profile among a plurality of predetermined profiles based on the shape or size of the person's breast, wherein each of the plurality of 3D-beam modulation filters are generated for only one of the plurality of predetermined profiles, wherein each of the plurality of immobilizers are generated for only one of the plurality of predetermined profiles.

6. The method of claim 1 wherein the selected 3D-beam modulation filter comprises a combined filter, the method further comprising:
selecting a bowtie-shaped filter among a plurality of bowtie-shaped filters based on the breast volume class assigned to the person's breast;
selecting a wedge-shaped filter among a plurality of wedge-shaped filters based on the breast volume class assigned to the person's breast; and
combining the selected bowtie-shaped filter with the selected wedge-shaped filter into the combined filter.

7. The method of claim 1, wherein coupling the selected immobilizer to the scanner system further comprises:
attaching a first end of an attachment element to a surface of the scanner system, and
attaching second end of the attachment element to the selected immobilizer.

8. The method of claim 7, wherein the attachment element includes a flange or a fastener.

9. The method of claim 1, further comprising:
acquiring two orthogonal scout views of the person's breast;
adjusting a position of at least one of the 3D-beam modulation filter and the person's breast based on the acquired orthogonal scout views of the person's breast.

10. A computing device including a non-transitory storage medium storing instructions, and a processor executing the instructions stored on the non-transitory storage medium to perform the method of claim 1.

11. A computed tomography (CT) scanner system, comprising:
an x-ray production system including an x-ray source configured to emit x-rays;
an x-ray detector system constructed and arranged to receive the x-rays emitted by the x-ray source;
a filter positioning system configured to select a 3D-beam modulation filter among a plurality of 3D-beam modulation filters each corresponding to a different breast volume class in a plurality of breast volume classes, said selected 3D-beam modulation filter corresponding to a breast volume class assigned to a body part to be imaged, said assigning based on at least one of a shape and a size of the body part, and further configured to position the selected 3D-beam modulation filter between the x-ray source and the x-ray detector system, wherein each 3D-beam modulation filter has a three-dimensional shape corresponding to at least one of a size and a three-dimensional shape of one of said breast volume classes so as to equalize intensities of individual x-rays within an x-ray beam after said x-ray beam passes through the body part, and
wherein said plurality of breast volume classes are defined from a plurality of CT data sets of a plurality of persons, each breast volume class corresponding to a different range of breast volume percentile groups; and
a gantry assembly system including a table for receiving the body part.

12. The CT scanner system of claim 11 further comprising:
a scanner control computer coupled to the x-ray production system and the gantry assembly system for sending control signals to the x-ray production system and the gantry assembly system.

13. The CT scanner system of claim 11, wherein the selected 3D-beam modulation filter comprises a combined filter, wherein the filter positioning system is further configured to:
select a bowtie-shaped filter among a plurality of bowtie-shaped filters based on the volume class assigned to said body part;
select a wedge-shaped filter among a plurality of wedge-shaped filters based on the volume class assigned to said body part; and
combine the selected bowtie-shaped filter and the selected wedge-shaped filter into the combined filter.

14. The CT scanner system of claim 11 further comprising:
an image acquisition computer for receiving image data from the x-ray detector system;
an image reconstruction computer for reconstructing a CT image of the body part based on the image data received from the image acquisition computer; and
a display for displaying the reconstructed CT image of the body part.

15. The CT scanner system of claim 14, wherein the image reconstruction computer receives data from a scanner control computer and the image acquisition computer, the data including at least one of x-ray beam intensity data, x-ray beam emission timing data, gantry assembly system positioning data, and projection images of the body part being imaged.

16. The CT scanner system of claim 11, wherein the body part is a breast and the selected 3D-beam modulation filter is configured to reduce a dose of radiation toward anterior and peripheral regions of the breast based on at least one of a shape and a size of the volume class assigned to the breast.

17. The CT scanner system of claim 11, further comprising an immobilizer coupled to the gantry assembly system, wherein the immobilizer is coupled to the gantry assembly system using one or more attachment elements.

18. The CT scanner system of claim 11, further comprising an immobilizer selection system configured to select a breast immobilizer from a plurality of breast immobilizers, each breast immobilizer corresponding to a different breast volume class out of the plurality of breast volume classes, each immobilizer structured to be connectable to and disconnectable from said table.

19. The CT scanner system of claim 18, further comprising said plurality of breast immobilizers.

20. The CT scanner system of claim 18, wherein the immobilizer selection system is further configured to position the person's breast in the selected immobilizer and perform a check for the immobilizer fit with a laser-based system.

21. The CT scanner system of claim 11, further comprising said plurality of 3D-beam modulation filters.

22. The CT scanner system of claim 11, wherein said filter positioning system is further configured to receive scout view data of the body part and to dynamically a position of at least one of the selected 3D-beam modulation filter and the body part, based on the scout view data and at least one of the shape of the body part, the size of the body part, and the assigned breast volume class.

23. The CT scanner system of claim 22, wherein said scout view data is x-ray scout view data.

24. The CT scanner system of claim 22, wherein said scout view data is optical scout view data.

25. The CT scanner system of claim 11, further comprising a laser-evaluating system configured to determine the breast volume class that best fits the person's breast.

26. A cone-beam breast computed tomography (CT) system, comprising:
a table arranged to support a person to lie prone with the person's breast extending through an aperture defined by the table;
a plurality of breast immobilizers, each corresponding to a different breast volume class out of a corresponding plurality of breast volume classes, each breast immobilizer structured to be connectable to and disconnectable from said table at said aperture to immobilize said person's breast when it extends through said aperture;
a gantry disposed proximate to said table;
a cone-beam x-ray source attached to said gantry and positioned to be able to irradiate said person's breast with a cone beam of x-rays;
a plurality of modulation filters, each corresponding to one of said plurality of breast volume classes, and each adapted to be connected to and disconnected from said gantry at a position between said cone-beam x-ray source and said person's breast; and
a flat-panel detector attached to said gantry and positioned to be able to receive at least a portion of said cone beam of x-rays after passing through said person's breast,
wherein said gantry is rotatable about an axis that intercepts said person's breast such that said cone-beam x-ray source and said flat-panel detector rotate with said gantry in unison, and
wherein said plurality of breast volume classes are defined from a plurality of CT data sets of a plurality of persons, each breast volume class corresponding to a different range of breast volume percentile groups, and
wherein at least one modulation filter of said plurality of modulation filters is a 3D-beam modulation filter that has a three-dimensional shape corresponding to at least one of a size and a three-dimensional shape of one of said breast volume classes so as to equalize intensities of individual x-rays within an x-ray beam after said x-ray beam passes through said person's breast.

27. The cone-beam breast computed tomography (CT) system according to claim 26,
wherein each said modulation filter compensates for different x-ray path lengths through different portions of said person's breast of the corresponding breast volume class to reduce a total amount of x-ray dose,
wherein each said modulation filter, when connected to said gantry, is rotatable with said gantry in unison with said cone-beam x-ray source and said flat-panel detector.

28. An accessory kit for a cone-beam breast computed tomography (CT) system, comprising:
a plurality of breast immobilizers, each corresponding to a different breast volume class out of a corresponding plurality of breast volume classes, and each being structured to be connectable to and disconnectable from a table of said cone-beam breast CT system at an aperture defined by said table; and
a plurality of modulation filters, each corresponding to a different breast volume class out of the corresponding plurality of breast volume classes, and each adapted to be connected to and disconnected from a gantry at a position between a cone-beam x-ray source and said person's breast,
wherein the plurality of breast volume classes are defined from a plurality of CT data sets of a plurality of persons, each breast volume class corresponding to a different range of breast volume percentile groups,
wherein each breast immobilizer is configured to immobilize a person's breast when it extends through said aperture, and
wherein at least one modulation filter of said plurality of modulation filters is a 3D-beam modulation filter that has a three-dimensional shape corresponding to at least one of a size and a three-dimensional shape of one of said breast volume classes so as to equalize intensities of individual x-rays within an x-ray beam after said x-ray beam passes through said person's breast.

29. The accessory kit according to claim 28, further comprising:
wherein each said modulation filter compensates for different x-ray path lengths through different portions of said person's breast of the corresponding breast volume class to reduce a total amount of x-ray dose,
wherein each said modulation filter, when connected to said gantry, is rotatable with said gantry in unison with said cone-beam x-ray source and a flat-panel detector.

30. An accessory kit for a cone-beam breast computed tomography (CT) system, comprising:
a plurality of modulation filters, each corresponding to a different breast volume class out of a corresponding plurality of breast volume classes, and each adapted to be connected to and disconnected from a gantry at a position between a cone-beam x-ray source and a person's breast,
wherein the plurality of breast volume classes are defined from a plurality of CT data sets of a plurality of persons, each breast volume class corresponding to a different range of breast volume percentile groups,
wherein each said modulation filter compensates for different x-ray path lengths through different portions of said person's breast of the corresponding breast volume class to reduce a total amount of x-ray dose,
wherein each said modulation filter, when connected to said gantry, is rotatable with said gantry in unison with said cone-beam x-ray source and a flat-panel detector, and
wherein at least one modulation filter of said plurality of modulation filters is a 3D-beam modulation filter that has a three-dimensional shape corresponding to at least one of a size and a three-dimensional shape of one of said breast volume classes so as to equalize intensities of individual x-rays within an x-ray beam after said x-ray beam passes through said person's breast.

31. The accessory kit according to claim 30, wherein each modulation filter of said plurality of modulation filters comprises a first filter for filtering along a first dimension and a second filter for filtering along a second dimension that is orthogonal to the first dimension.

32. The accessory kit according to claim 31, wherein at least one of said first filter or said second filter is formed from titanium.

* * * * *